(12) United States Patent
Bacon et al.

(10) Patent No.: US 7,036,505 B2
(45) Date of Patent: May 2, 2006

(54) DISPENSER

(75) Inventors: Raymond John Bacon, Hampshire (GB); Iain Grierson McDerment, Hertfordshire (GB)

(73) Assignee: Clinical Designs Ltd., Aldsworth Emsworth (GB)

( * ) Notice: Subject to any disclaimer, the term of this patent is extended or adjusted under 35 U.S.C. 154(b) by 76 days.

(21) Appl. No.: 10/333,891

(22) PCT Filed: Jul. 24, 2001

(86) PCT No.: PCT/GB01/03313

§ 371 (c)(1),
(2), (4) Date: Apr. 11, 2003

(87) PCT Pub. No.: WO02/11802

PCT Pub. Date: Feb. 14, 2002

(65) Prior Publication Data

US 2003/0150448 A1 Aug. 14, 2003

(30) Foreign Application Priority Data

Jul. 24, 2000 (GB) .................................. 0018051.3
Sep. 20, 2000 (GB) .................................. 0023024.3

(51) Int. Cl.
*A61M 16/00* (2006.01)

(52) U.S. Cl. ..................... 128/203.13; 128/203.15; 128/200.14; 604/58

(58) Field of Classification Search .......... 128/200.14, 128/200.23, 203.12, 203.15, 203.17, 203.26, 128/203.27, 203.28, 204.27, 204.26, 205.25; 604/58

See application file for complete search history.

(56) References Cited

U.S. PATENT DOCUMENTS

| 3,012,454 | A | * | 12/1961 | Brodbeck | ................ 198/803.7 |
| 3,181,743 | A | * | 5/1965 | Libit et al. | .................. 222/528 |
| 4,576,157 | A | | 3/1986 | Raghuprasad | |
| 4,664,107 | A | | 5/1987 | Wass | |
| 5,069,204 | A | * | 12/1991 | Smith et al. | ........... 128/200.23 |
| 5,113,855 | A | * | 5/1992 | Newhouse | ............. 128/203.12 |
| 5,224,472 | A | | 7/1993 | Pesenti et al. | |
| 5,447,150 | A | | 9/1995 | Bacon | |

(Continued)

FOREIGN PATENT DOCUMENTS

GB 997617 7/1965

(Continued)

*Primary Examiner*—Glenn K. Dawson
*Assistant Examiner*—Michael Mendoza
(74) *Attorney, Agent, or Firm*—Alfred A. Fressola; Ware, Fressola, Van Der Sluys & Adolphson, LLP

(57) ABSTRACT

A dispenser has a body 201 with a mouthpiece 202 and a pivoted mouthpiece cover 203. The mouthpiece is formed as an aperture 2021 in a separate body part 2012 clipped to a main body part 2011. The mouthpiece part is cut away 2014 with respect to the medicament can 211 fitted to the body to define an air inlet exposed by the cover when this is open. The cover is pivoted about an axis 204 low in the body at the joint between the two body parts. Integrally moulded with the cover 203 is a half round shaft 2031, which carries a cam arrangement 205 comprising a pair of cam lobes 2051, 2052 and an intermediate shaft 2053. The can 211 is held in an opening 210 at the upper end of the main body part 2011 by a pair of location pins 2101 in openings 2102 in sidewalls of the body part. A junction member 217 is slidably accommodated in the body with the ribs engaging in grooves 218 in its periphery.

41 Claims, 16 Drawing Sheets

U.S. PATENT DOCUMENTS

| | | | | |
|---|---|---|---|---|
| 5,469,843 A | * | 11/1995 | Hodson | 128/203.15 |
| 5,655,523 A | * | 8/1997 | Hodson et al. | 128/203.15 |
| 5,740,793 A | * | 4/1998 | Hodson et al. | 128/203.15 |
| 6,422,234 B1 | * | 7/2002 | Bacon | 128/200.14 |

FOREIGN PATENT DOCUMENTS

| | | |
|---|---|---|
| WO | 9841254 | 9/1998 |
| WO | 9852634 | 11/1998 |

\* cited by examiner

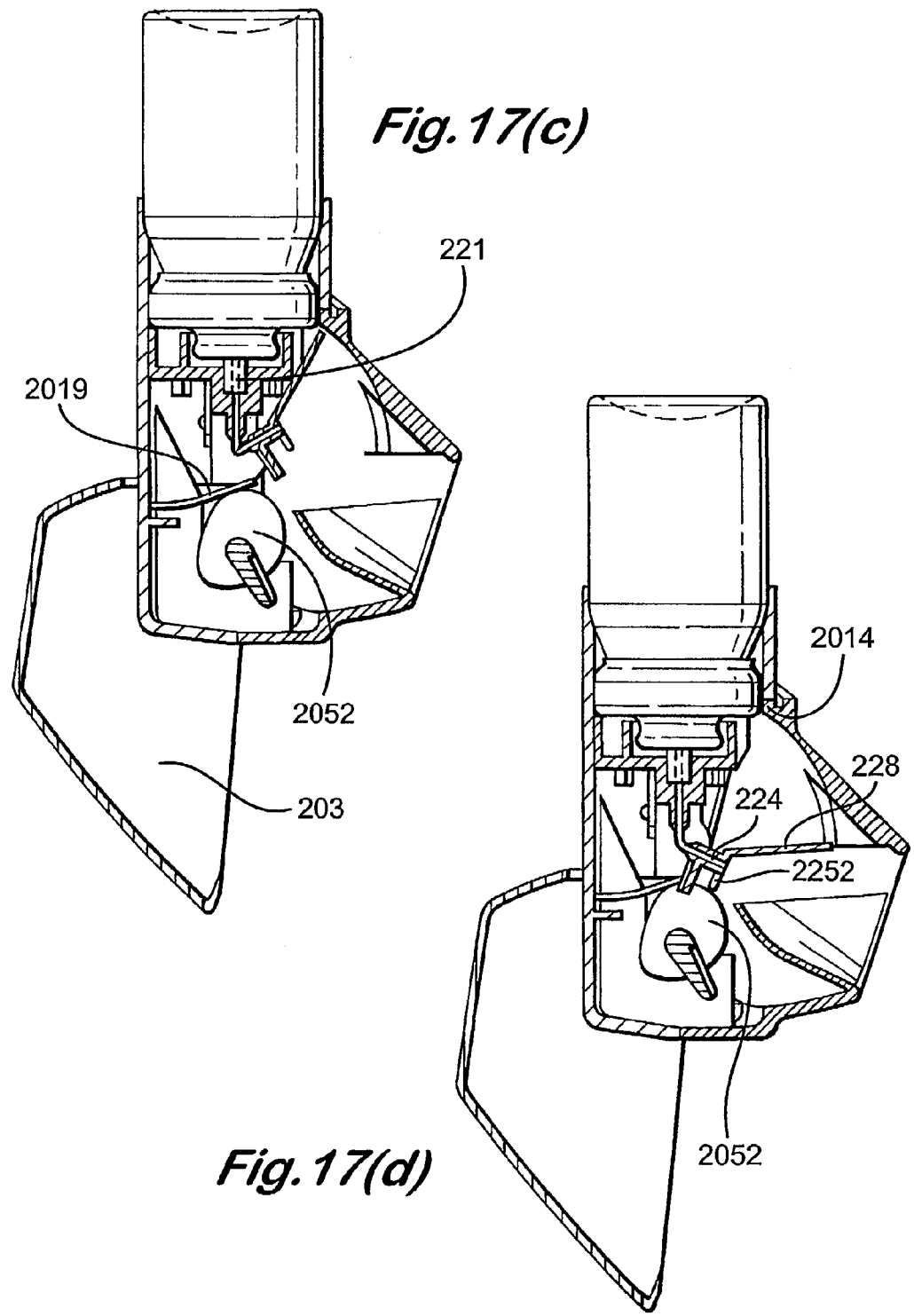

DISPENSER

CROSS REFERENCE TO RELATED APPLICATIONS

This application is for entry into the U.S. national phase under §371 for International Application No. PCT/GB01/03313 having an international filing date of Jul. 24, 2001, and from which priority is claimed under all applicable sections of Title 35 of the United States Code including, but not limited to, Sections 120, 363 and 365(c), and which in turn claims priority under 35 USC §119 to Great Britain Patent Application No. 0023024.3 filed on Sep. 20, 2000 and Great Britain Patent Application No. 0018051.3 filed on Jul. 24, 2000.

TECHNICAL FIELD

The present invention relates to a dispenser, particularly though not exclusively for dispensing aerosol or powder borne medicaments.

BACKGROUND OF THE INVENTION

In my prior International Patent Application, PCT/GB98/00770, at least as amended on entry in the European Regional Phase, there is described and claimed:

A dispenser for a gaseous, gas borne or droplet substance, the dispenser including:
- a body having a mouthpiece with an inhalation/insufflation orifice at its end;
- a junction in the body for a source of gas or evaporable liquid comprising or containing the said substance (the source being carried by the body); and
- a breath actuable valve, for controlling the release of said gas or liquid, comprising:
    - a valve inlet connected to the junction;
    - a valve outlet;
    - a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
    - a movable member, for moving the movable portion of the tube to control its kinking, and being movably mounted in the body for movement by the act of inhalation from a rest position towards the orifice—or at least in the direction of air flow through the dispenser;
- the tube being kinked to an obturating extent when the movable member is in a rest position and un-kinked when the movable member is moved on inhalation for release of the gas or liquid.

Such a dispenser can loosely be classed as a breath actuated, kink valve dispenser and is referred to herein as "My Earlier Breath Actuated, Kink Valve Dispenser".

The main embodiments of My Earlier Breath Actuated, Kink Valve Dispenser included a piston acted on by a differential breath induced pressure. The resultant force generated is generally sufficient to operate the dispenser by drawing the piston towards the dispenser's mouthpiece and extending and opening the kink valve. Nevertheless, I feel that the dispenser is susceptible of some improvement.

SUMMARY OF THE INVENTION

The object of the present invention is to provide improved breath actuated, kink valve dispensers According to one aspect of the invention I provide a dispenser for a gaseous, gas borne or droplet substance contained in a source thereof, the dispenser including:
- a body with a mouthpiece;
- a junction member in the body for the substance source; and
- a breath actuable valve, for controlling the release of the gas or liquid containing or comprising the substance, the valve comprising:
    - a flexible tube for receiving the said gas or liquid, the tube extending from a valve inlet connected to the junction member and having a portion which is kinkable for closure of the valve and movable to an open position in which the tube is un-kinked for opening of the valve; and
    - a member arranged for movement in the body by inhalation to un-kink the valve;
- the tube being kinked to an obturating extent when the movable member is in a ready position and un-kinked when the movable member is moved on inhalation for release of the gas or liquid;

wherein:
- the movable member is or includes a flap arranged in the body for action of breath on it on inhalation;
- the junction member, the flexible tube and the movable flap are a single injection moulding of plastics material; and
- the movable flap is pivotally connected to the junction member.

Preferably, wherein the movable flap is pivotally connected to the junction member by a living hinge which is an integral part of the single injection moulding.

Preferably, the junction member is slidably mounted in the body for movement in a direction for dispensing a dose of the substance from the source and the dispenser includes:
- means for pivoting the flap to its ready position on or prior to initial movement of the junction member and
- junction member resilient means for returning the junction member after release of the dose.

Normally the dispenser includes means to hold the flap in its ready position prior to inhalation movement to un-kink the valve and in particular an over-centre mechanism. This can comprise a lug and a spring, both integrally moulded with the said single injection moulding, one with the junction member and the other with the flap, the lug being integrally moulded with the flap for pivotal movement with it about the living hinge and the spring being integrally moulded with the junction member. Conveniently the spring is a leaf spring normally urging the flap to an open position of the valve and urging the flap to its ready position when passed over-centre to this position.

Normally, the single injection moulding is provided with formations guiding it for movement in the body. Alternatively, the single injection moulding can be mounted in a carrier provided with formations guiding it for movement in the body.

In one embodiment, both the source and the single injection moulding, including the junction member (and the carrier where provided), are translationally mounted in the body for movement by depression of the source towards the body, and the junction member resilient means acts against the body, accommodates the movement of the junction member resulting in the pivoting of the flap, limits the junction member's movement on further movement of the source with respect to the junction member for dispensing of a dose and returns the junction member (and the source) on release of pressure on the source. In this embodiment, the flap pivoting means comprises:

an actuator having:
an first abutment movably mounted with respect to the body and against which the flap is pressed for pivotal movement thereof on initial movement of the junction member (and the source) moving the flap against the first abutment;
a second abutment for disengaging the first abutment from the flap, the second abutment being connected to the first abutment, movably mounted with respect to the body, and arranged to abut the source and move it on its said further movement; and
abutment resilient means acting against the body, accommodating the said further movement of the source and the second abutment abutted against it, limiting said further movement on dispensing of the dose and returning the abutments on release of pressure on the source.

Preferably, the actuator is another single injection moulding; and the first abutment is so positioned as to limit the movement of the flap on releasing of the dose that the outlet of the flexible tube is directed out of the mouthpiece.

In other embodiments, the junction member resilient means is a spring in the source and the dispenser includes:
means for locating the source in the body with the junction member being slidable towards it and
means for displacing the junction member towards the source for dispensing the dose into the kinked tube.

The means for displacing the junction member can comprise:
a button arranged on the body opposite the source and movable towards the source with abutment against the junction member and with compression of the spring in the source and
the means for pivoting the flap is an actuator having:
an first abutment movable with the button against the flap for pivotal movement of the flap on initial movement of the button;
a second abutment movable with the first abutment against a fixed point in the dispenser for limiting the movement of the first abutment member and
a spring acting between the button and the abutments for causing the limited movement of the latter on movement of the button and allowing further movement of the button for movement of the junction member for dispensing a dose into the tube kinked on its pivotal movement.

Preferably the abutments are so arranged that the first abutment is moved at the end of its limited movement to a position in which it acts as a stop for the flap on its return pivotal movement for release of the dose on inhalation.

Alternatively, the means for displacing the junction member can comprise:
a grippable member rotatably arranged on the body and
a rotary-to-linear motion conversion mechanism, arranged to convert rotary motion of the grippable member to linear motion for displacing the junction member towards the source and the means for pivoting the flap is incorporated in the motion conversion mechanism.

Again, the grippable member is preferably a cocking lever.

In accordance with an important preferred feature, the cocking lever is a cover for the mouthpiece prior to dispensing of a dose from the source, a dose being dispensed to the kink valve on opening of the cover.

Preferably, the cocking lever incorporates a main cam comprising the motion conversion mechanism in co-operation with the junction member and/or the carrier where provided; and means for pivoting the flap is a secondary cam mechanism acting between the cocking lever and the flap. The secondary cam mechanism can comprise a finger on the cam of the cocking lever and a finger on the flap, the fingers engaging as the cocking lever is opened to move the flap to its ready position. Conveniently, the fingers are shaped to deflect away from each other on return movement of the cocking lever, with the flap in its position corresponding to the valve being open.

The dispenser can include a tertiary cam mechanism for returning the flap to its valve open position on return movement of the cocking lever; and the tertiary cam mechanism can comprise a finger on the cocking lever and a finger on the flap, the fingers engaging as the cover is closed to move the flap to its valve open position (if not already in this position).

In accordance with particular features:

the body includes one or more webs extending between the main cam and the movable junction member for reacting lateral cam force and transmitting longitudinal cam force to the movable junction member and/or the carrier where provided;

the cocking lever includes a shaft having the main cam formed thereon, the shaft being of hollow half-round configuration and body includes at least one partially open journal for the half-round shaft;

the body includes a secondary body part attachable to a main body part to provide the mouthpiece and an air inlet between the two parts.

A particular object is the provision of spring assistance to open the kink valve.

Accordingly in another aspect of the invention I provide a dispenser for a gaseous, gas borne or droplet substance contained in a source thereof, the dispenser including in common with My Earlier Breath Actuated, Kink Valve Dispenser:

a body with a mouthpiece;

a junction in the body for the substance source; and a breath actuable valve, for controlling the release of the gas or liquid containing or comprising the substance, the valve comprising:

a flexible tube for receiving the said gas or liquid, the tube extending from a valve inlet connected to the junction and having a portion which is kinkable for closure of the valve and movable to an open position in which the tube is un-kinked for opening of the valve; and a member arranged for movement in the body by inhalation to un-kink the valve;

the tube being kinked to an obturating extent when the movable member is in a ready position and un-kinked when the movable member is moved on inhalation for release of the gas or liquid;

the dispenser also including:

a spring for assisting the movement to un-kink the tube and means to hold the movable member in the ready position to close the tube by kinking prior to inhalation.

The holding means may be frictional means holding the movable member ready for release and released by overcoming the frictional force holding the movable member in its ready position.

However, in the preferred embodiment of this aspect, the holding means is a mounting of the movable member in an over-centre manner with respect to the spring, whereby the spring acts to urge the movable member into the ready position when close to this position, and away from it when the inhalation force on the movable member causes the spring to pass over-centre after a small movement of the movable member to assist in the un-kinking.

Further, in this embodiment, there is a cocking mechanism to move the movable member to its over-centre position in which the tube is kinked. The cocking mechanism can be actuated from a manually movable knob or the like. However, it is preferably actuated by the same movement of the substance source, usually an aerosol container, which releases a dose of the substance into the kinked tube. With such an arrangement, the tube reaches its kinked state immediately prior to the movable member moving to the over-centre position and the substance dose being released.

This arrangement has the advantage of the usual state of the spring being unloaded and the usual state of the tube being un-kinked. Since both of these are preferably of synthetic material, which tends to be prone to stress relaxation, this arrangement assists reliable operation of the dispenser.

I can envisage the movable member being translationally mounted in the body, as in the preferred embodiments of my International Application PCT/GB98/00770, on My Earlier Breath Actuated, Kink Valve Dispenser. However, it is preferably pivotally mounted. This can be directly about an pivot fixed in the body. However, the pivot is normally provided on a carrier, itself translationally mounted in the body. Where the movable member is pivotally mounted, a stop is preferably provided for stopping it in a position in which an outlet from the tube points directly out of the mouthpiece.

Whereas in my earlier International Application, usually the kink valve is normally closed and opened only for dispensing, although in one embodiment it is normally open and closed only for dispensing; in the present invention the kink valve is normally open. Nevertheless, I can envisage that it could be normally closed, being opened for dispensing and closed again thereafter.

In another aspect of the invention, I provide a dispenser for a gaseous, gas borne or droplet substance contained in a source thereof having an outlet movable for release of the substance, the dispenser comprising:

- a body with a mouthpiece;
- a rigid connection between the body and the source;
- a substance junction movably arranged in the body for the substance outlet;
- a breath actuatable mechanism for controlling the dispensing of the gas or liquid containing or comprising the substance from the substance outlet to the mouthpiece; and
- a cocking lever for cocking the breath actuatable mechanism.

It is envisaged that the breath actuatable mechanism may be a spring mechanism cocked by the cocking lever to load the spring and released by breath actuation to cause the spring to depress the substance outlet and release the substance directly towards the mouthpiece. However, in the preferred embodiment, the breath actuatable mechanism is a breath actuatable valve and the cocking lever is arranged to cock the valve and depress the substance outlet, conveniently via depression of the substance junction, for release of the substance to the valve, the breath actuatable valve having:

- an inlet connected to the junction,
- a valve closure for retaining released substance prior to breath actuation and
- an outlet for directing the substance to the mouthpiece for inhalation.

Normally the source of the substance will include a metered dose valve, whereby it will release a metered dose each time the dispenser is operated.

Whilst it can be envisaged that, where the source is adapted for it, the rigid connection between the source and the body may take the form of a bayonet connection or the like, in the preferred embodiment, the rigid connection is provided by detents engaging in a groove formed in a can of the source. Whilst the detents can be locked in position by a movable-cam locking member, it is preferred that they rely on the resilience of the body—of moulded plastics material—to retain the rigid connection of the body to the can.

Preferably the breath actuatable valve will be a kink valve whereby:

- the valve closure is a flexible tube for receiving the said gas or liquid, the tube extending from the valve inlet connected to the substance junction and having a portion which is kinkable for closure of the valve and movable to an open position in which the tube is un-kinked for opening of the valve; and
- the valve outlet is arranged for movement in the body on inhalation to unkink the valve;
- the tube being kinked to an obturating extent when the outlet movable member is in a ready position and un-kinked when the outlet movable member is moved on inhalation for release of the gas or liquid.

Whilst the cocking lever can be envisaged to take other forms, such as a trigger squeezed when the dispenser is to be used, preferably it incorporates a cover for the mouthpiece, with the metered dose being released to the breath actuated valve when the cover is opened.

Preferably, the cover is pivotally connected to the body and incorporates a cam for lifting the outlet on opening of the cover. The substance outlet can be rigidly connected to the substance junction, and the cam conveniently acts on the latter.

In the preferred embodiment of this aspect, the valve outlet member is pivotally connected to the substance junction for movement between an open, un-kinked dispensing position and a closed, kinked position for retaining the metered dose. A secondary cam is provided for moving the outlet member to its closed position. For holding it there—prior to breath actuation—an over-centre spring is preferably provided.

In accordance with a fourth aspect of the invention, I provide a dispenser for a gaseous, gas borne or droplet substance contained in a source thereof, the dispenser including:

- a body with a mouthpiece;
- a junction member in the body for the substance source; and
- a breath actuable valve, for controlling the release of the gas or liquid containing or comprising the substance, the valve comprising:
  - a flexible tube for receiving the said gas or liquid, the tube extending from a valve inlet connected to the junction member and having a portion which is kinkable for closure of the valve and movable to an open position in which the tube is un-kinked for opening of the valve; and a member arranged for movement in the body by inhalation to un-kink the valve;

the tube being kinked to an obturating extent when the movable member is in a ready position and un-kinked when the movable member is moved on inhalation for release of the gas or liquid;

wherein:

the junction member is slidably mounted in the body for movement in a direction for dispensing a dose of the substance from the source against resilient urging of a spring in the source and the dispenser includes:

means for locating the source in the body with the junction member being slidable towards it, means for pivoting the flap to its ready position on or prior to initial movement of the junction member, a button arranged on the body opposite the source and movable towards the source with abutment against the junction member and with compression of the spring in the source for displacing the junction member towards the source for dispensing the dose into the kinked tube and an actuator having:

an first abutment movable with the button against the flap for pivotal movement of the flap on initial movement of the button;

a second abutment movable with the first abutment against a fixed point in the dispenser for limiting the movement of the first abutment member and a spring acting between the button and the abutments for causing the limited movement of the latter on movement of the button and allowing further movement of the button for movement of the junction member for dispensing a dose into the tube kinked on its pivotal movement.

In all embodiments, it is preferred that the source of the substance includes a metered dose valve, whereby it release a metered dose each time the dispenser is operated. However, it is specifically envisaged that the source can include a non-metered dose valve, the dose being metered by the capacity of the breath actuable valve.

BRIEF DESCRIPTION OF THE DRAWINGS

To help understanding of the invention, a specific embodiment thereof will now be described by way of example and with reference to the accompanying drawings, in which.

DETAILED DESCRIPTION

Figure 1A:
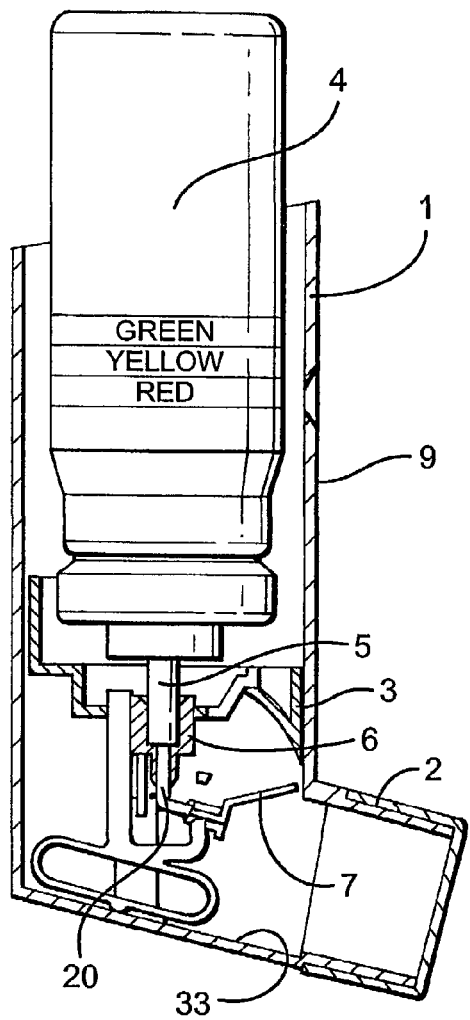
FIG. 1 shows in a series of cross-sectional side views (a) to (d) a dispenser according to the invention, in quiescent, cocked, charged and dispensed state.
Figure 1B:
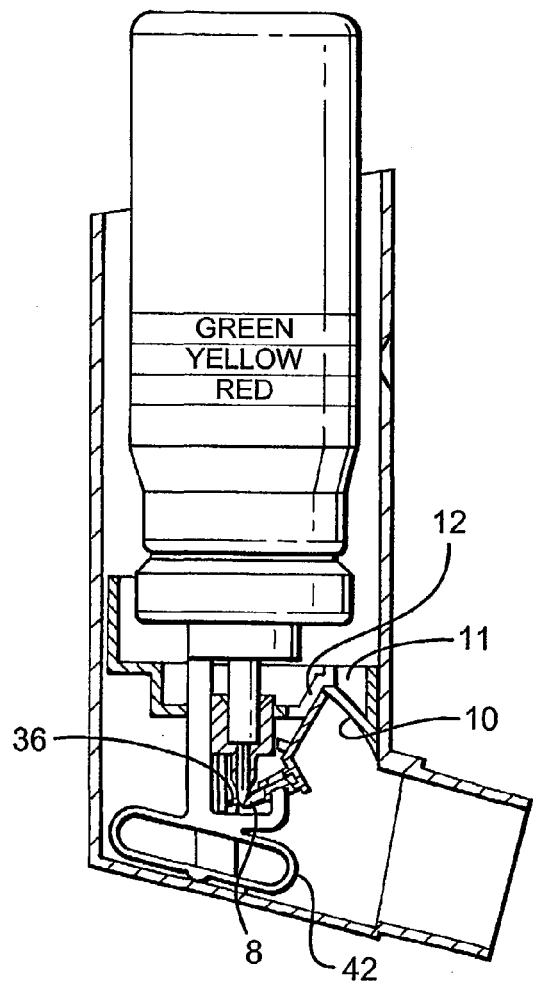
Figure 1C:
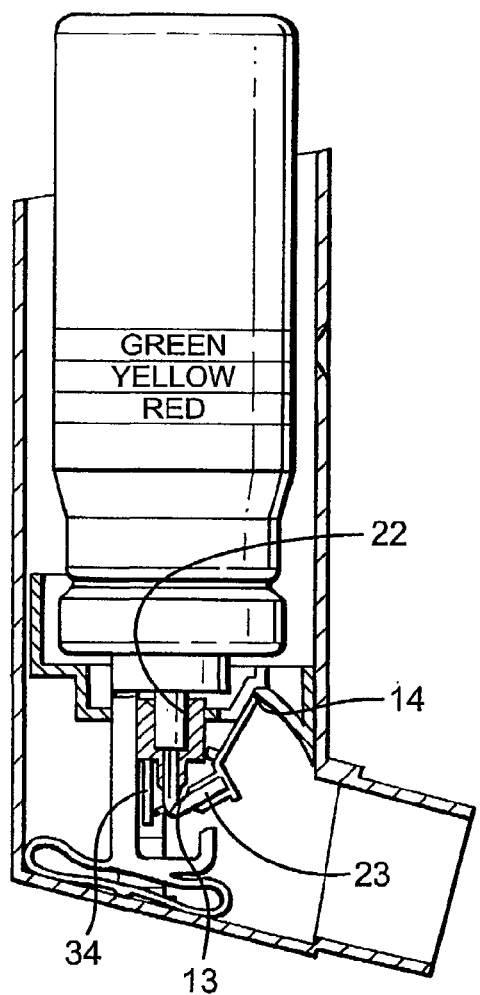
Figure 1D:
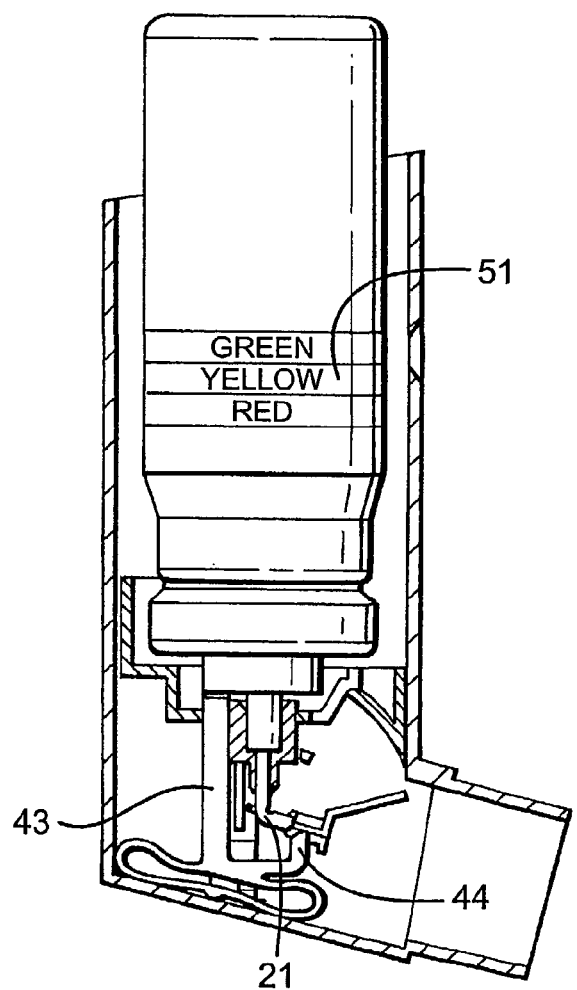
Figure 2:
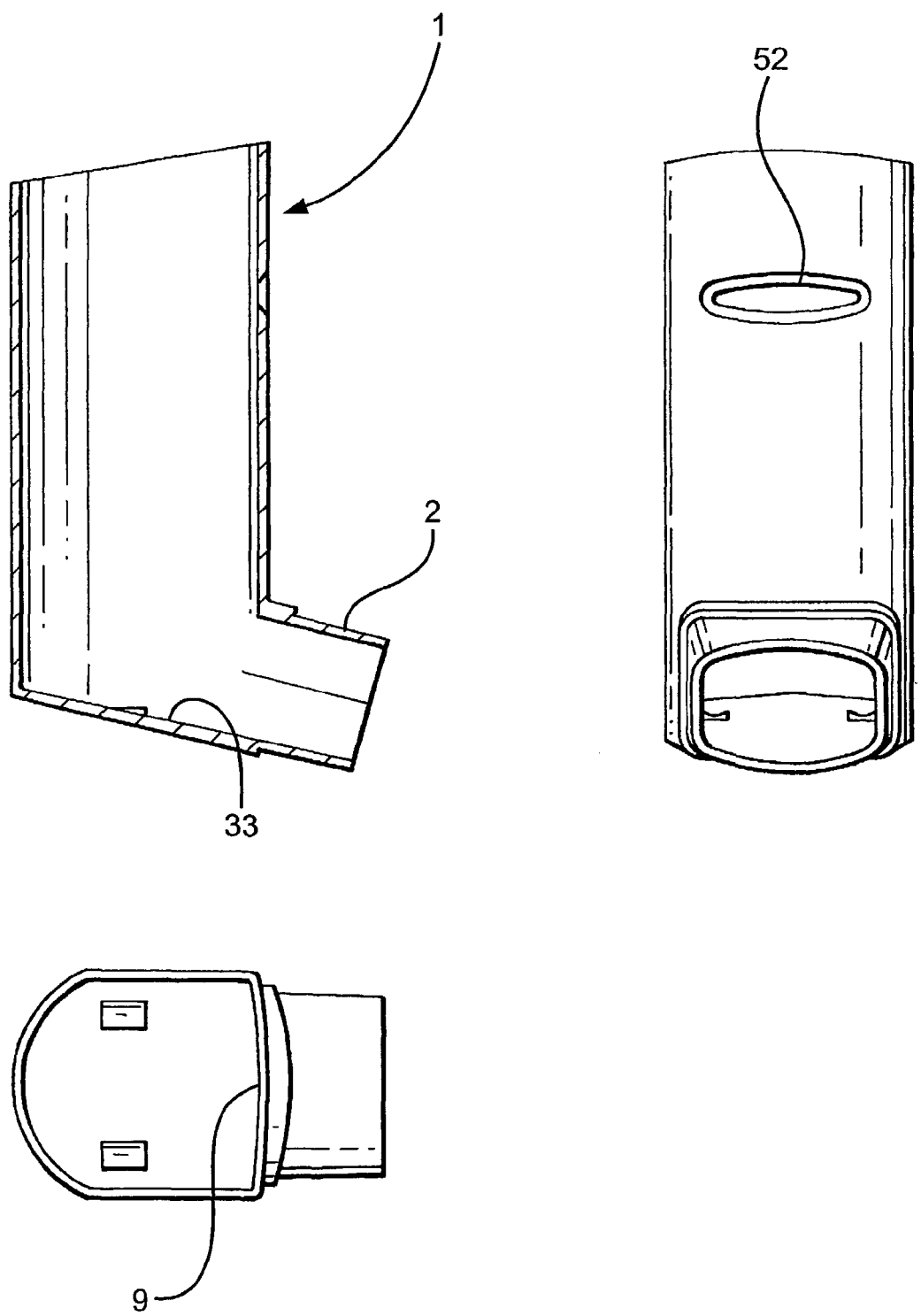
FIG. 2 shows various views of a body of the dispenser of FIG. 1.
Figure 3:
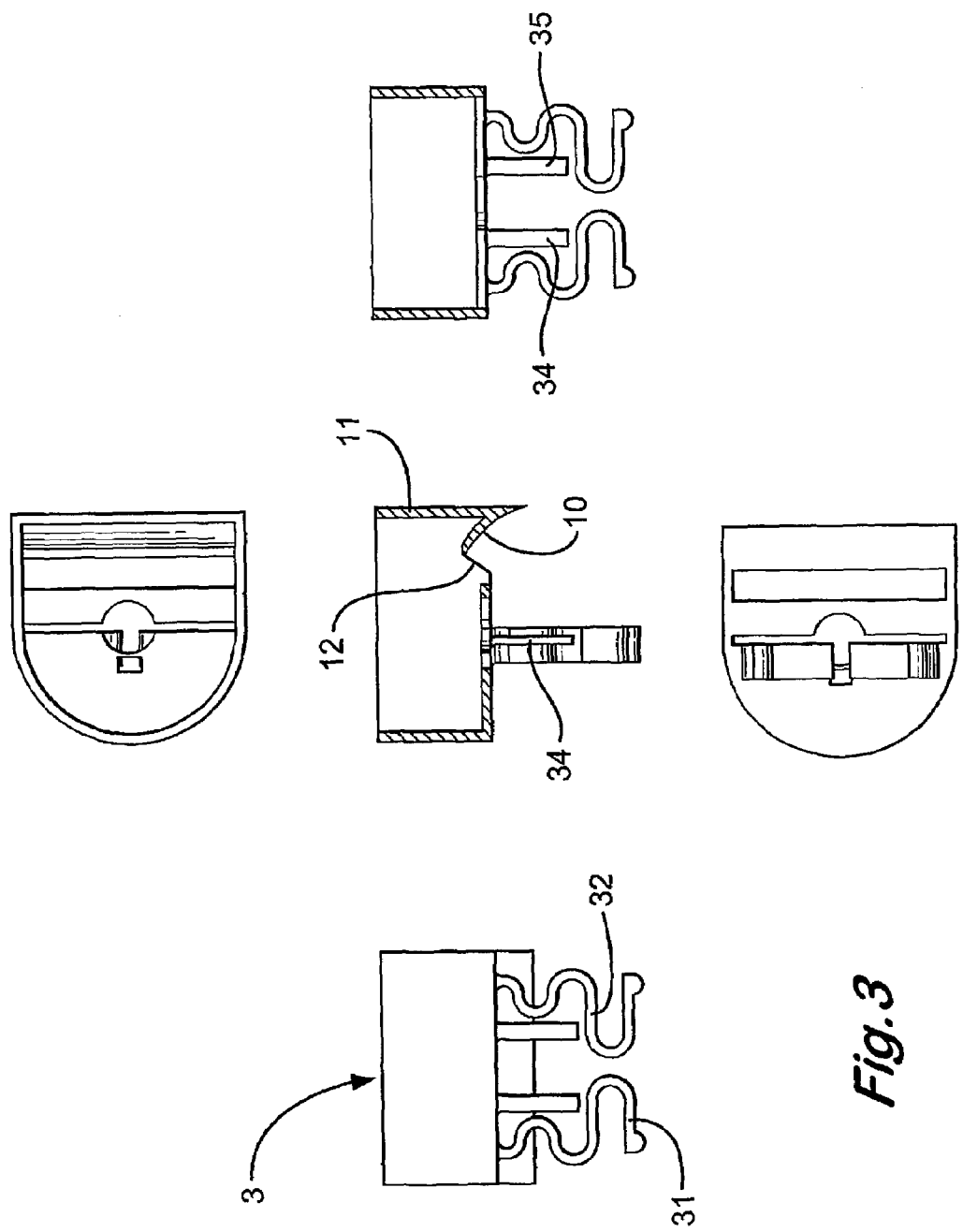
FIG. 3 shows in various views a carrier of the dispenser of FIG. 1.
Figure 4:
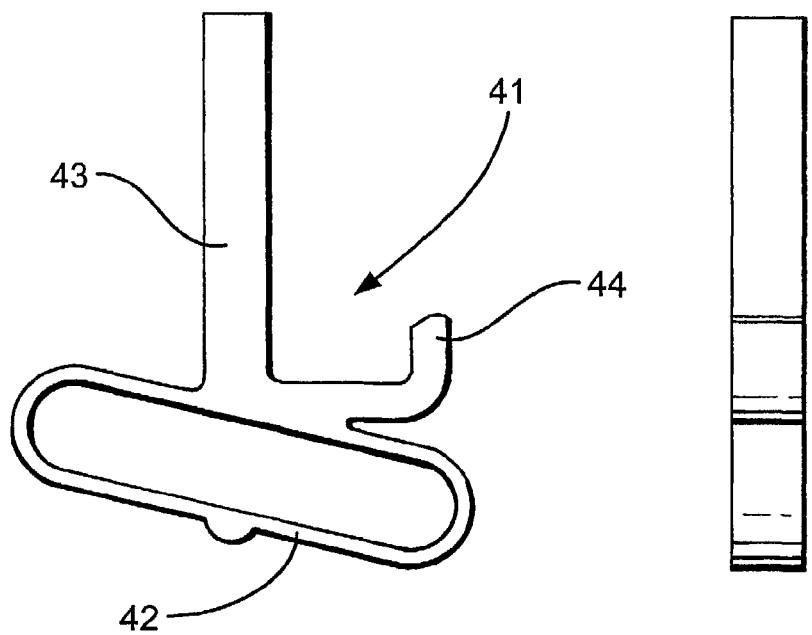
FIG. 4 shows in two views an actuator of the dispenser of FIG. 1.
Figure 5:
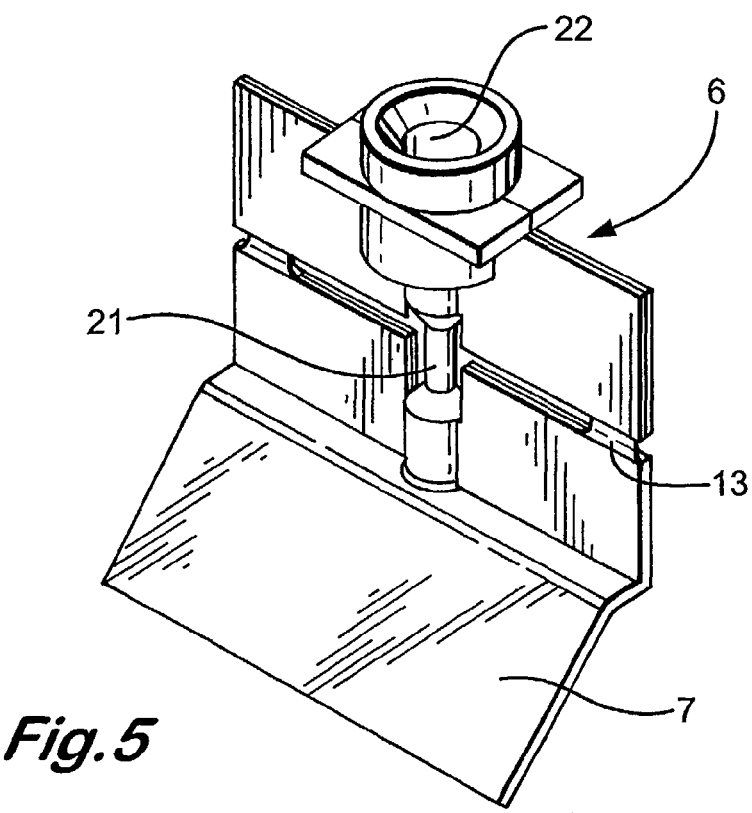
FIG. 5 is a perspective view of a receptor and flap valve of the dispenser of FIG. 1.
Figure 6:
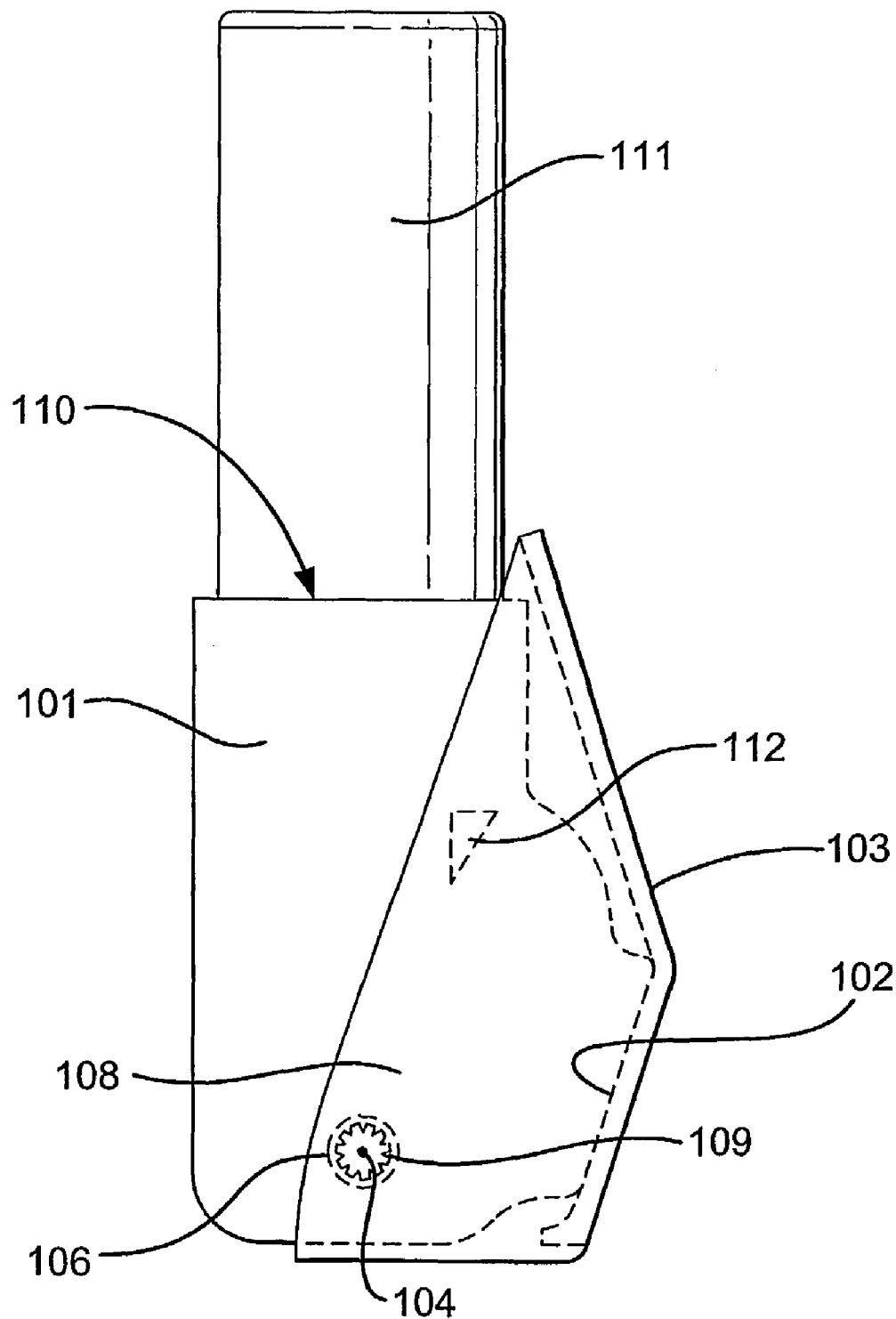
FIG. 6 is a side view of another dispenser of the invention.
Figure 7:
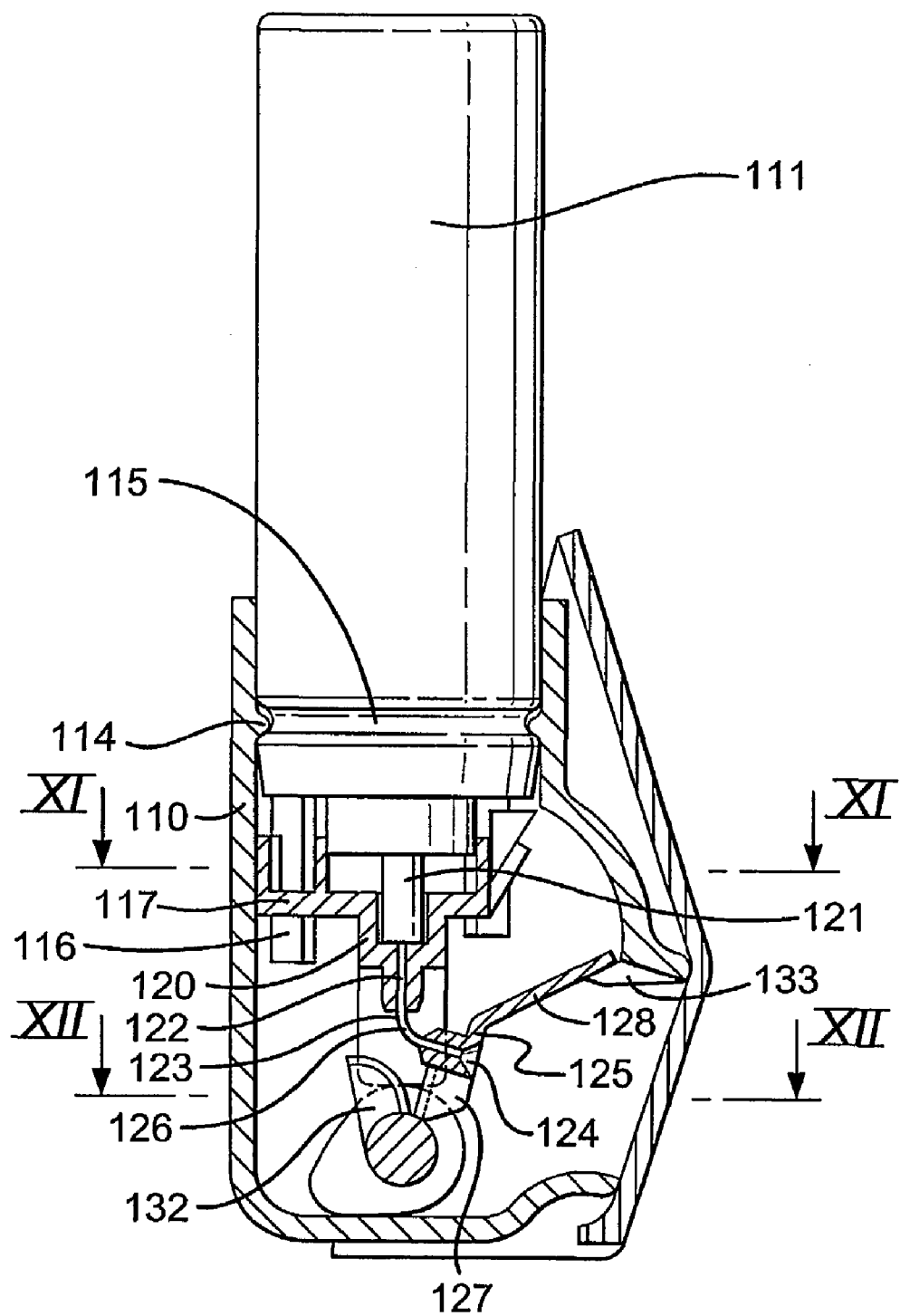
FIG. 7 is central cross-sectional side view of the dispenser of FIG. 6.
Figure 8:
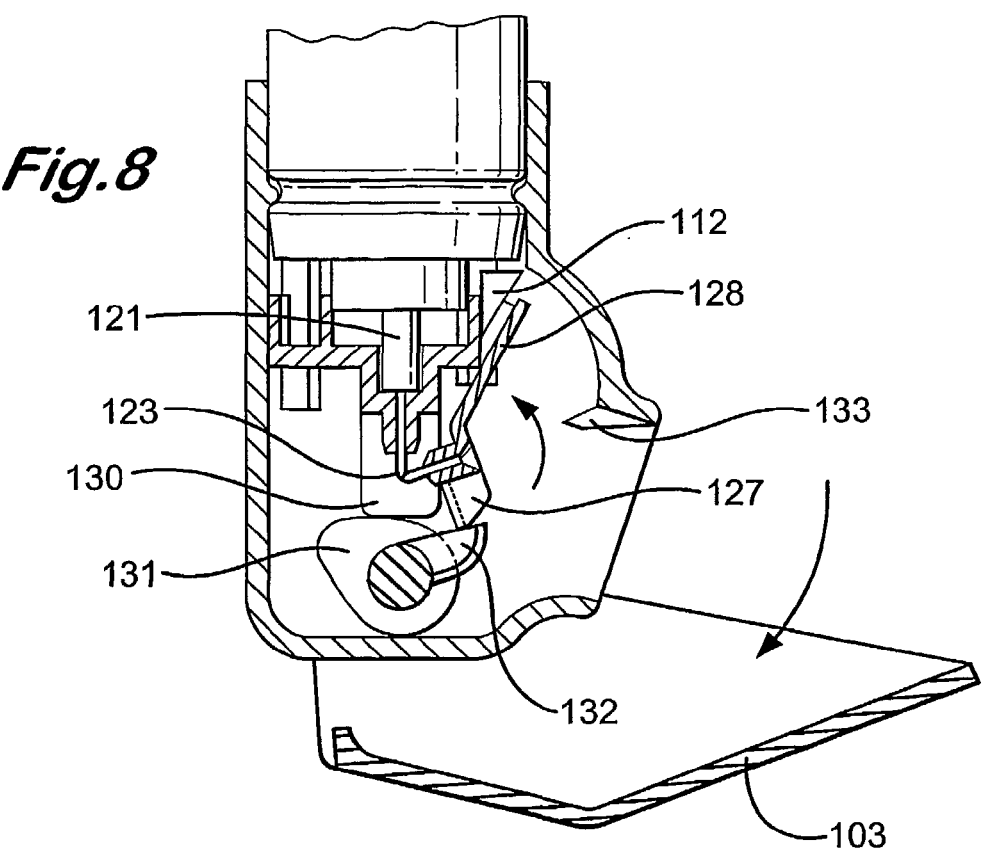
FIG. 8 is a view similar to FIG. 7 of the lower half of the dispenser, cocked but not yet primed is a metered dose.
Figure 9:
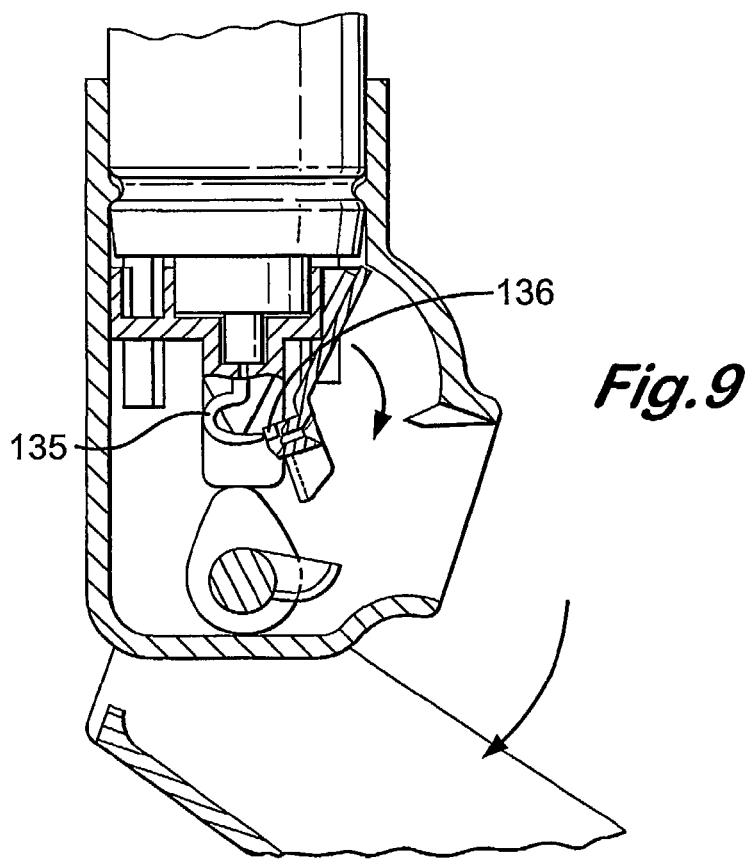
FIG. 9 is a similar view of the dispenser when primed.
Figure 10:
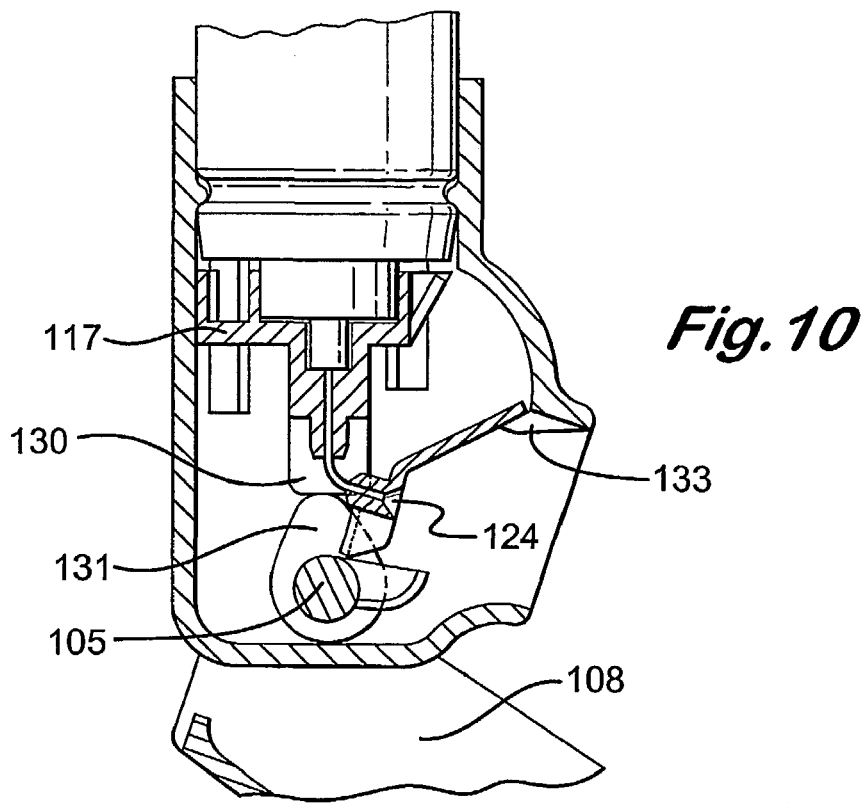
FIG. 10 is a similar view of the after breath actuation.
Figure 11:
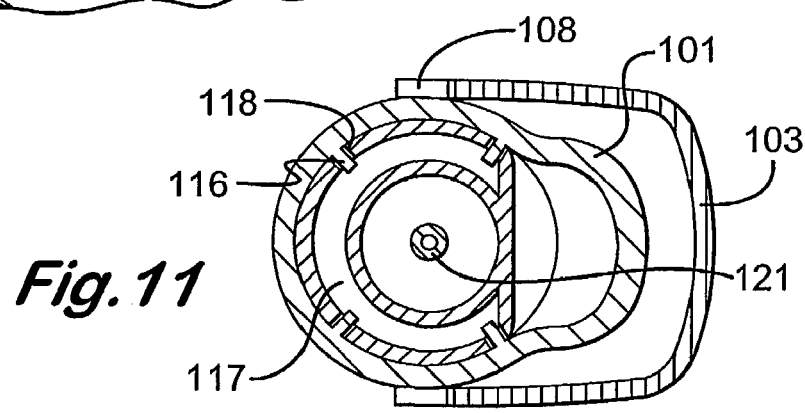
FIG. 11 is a cross-sectional view on the line XI—XI in FIG. 7.

Referring to the FIGS. 1 to 5, the breath actuated dispenser there-shown has a body 1 with a mouthpiece 2. Via a carrier 3, an aerosol drug can 4 is mounted in the body. The can has a dispensing spout 5, which engages a receptor moulding 6, the receptor moulding being engaged in the carrier and incorporating a breath movable flap 7 and a kink valve 8. The parts (other than the can) are of injection moulded plastics material.

The body has a D-shaped cross-section in plan, with the flat 9 of the D at the mouthpiece side 2. The carrier 3 is of complementary shape and arranged to closely fit in the body. It has a curved under-contour 10 on the flat side 11 and a slot 12 adjacent the inner end of the flap.

The movable flap 7 is connected to the main receptor moulding part by a living hinge 13 arranged at the centre of curvature of the contour 10, whereby the distal edge 14 of the flap can move with a small clearance from the contour.

The receptor is moulded with the flap angled down with respect to the use orientation and a linear passage 20 through it. The central portion 21 of the passage has a thin wall thickness, whereby when the flap is hinged up, the passage kinks and closes. The upper end 22 of the passage is of larger diameter to receive the spout of the can. The lower end of the passage forms a spray nozzle 23, which is directed in accordance with the angle of the flap.

The carrier has four depending springs. Two outer ones 31,32 are serpentine and of a length to abut a bottom 33 of the body and normally urge the carrier into its upper position. The two inner springs 34,35 are leaf springs, which abut a lug 36 on the flap for giving it an over-centre action.

An actuator 41 is arranged beneath the carrier. This has an oblong spring 42 and a pair of actuating fingers. The one 43 is abutted by the can on the latter's depression for use of the dispenser. The other 44 abuts the underside of the flap for setting it.

The action of the dispenser is as follows:

With the spout of the can engaged in the mouth of the receptor and the springs allowed to relax, the can projects out of the body. Depression of it moves the carrier down. The actuator spring 42 does not at first compress. Its shorter lug abuts the underside of the flap. The receptor is moving down and with it the hinge so that the flap is pivoted to rotate anticlockwise—as shown in FIG. 1. The lugs 36 of the flap abut the leaf springs 34,35 and are so arranged that when the flap has been rotated to a fully lifted position in which it engages the carrier, the springs are acting lightly to hold the flap up.

Further depression of the can causes the long finger 43 to abut the can and compress the oblong spring 42 of the actuator. This withdraws the short finger from contact with the flap valve. At this stage, the serpentine springs are exerting a greater upwards force on the carrier than that of the internal spring in the can pushing the spout outwards. It is pushed in, releasing a dose of its contents into the receptor's passage 20. The latter has now been closed by kinking of the central portion. The dispenser is ready for breath actuation.

Breathing in through the mouthpiece creates a pressure differential across the flap, which pivots down. The leaf spring and lug arrangement passes over-centre and the springs come to assist the opening action. It is stopped by abutment of the flap with the short finger 44. In this position, the nozzle 23 is directed in line with the mouthpiece and the valve has un-kinked. The dose is dispensed to be breathed in, with air now able to flow freely through the slot 12, past the end of the flap.

Release of the can allows the carrier to rise. The flap does not rotate, since there is nothing to cause it to do so.

The state of the mechanism is dependent upon the position of the can in its body. This can be seen by providing coloured bands 51 on the can and a window 52 in body.

This embodiment is not intended to be restricted to the details of the above described embodiment. For instance instead of the short finger 44, whose use position is determined by the degree of compression of the spring 42, a fixed stop moulded as an integral part of the body/mouthpiece may be provided at their junction for stopping the flap 7 with the nozzle 23 pointing directly out of the mouthpiece.

Referring to FIGS. 6 to 12, the dispenser thereshown has a body 101 with a mouthpiece 102 and a pivoted mouthpiece cover 103. The latter is pivoted about an axis 104 low in the body and carried on a cam member 105 journalled in the body at openings 106. The cover is connected irrotationally to end spigots 107 of the cam member at sides 108 of the cover. The spigots and the sides have respective angularly-uniquely formations 109, which determine the angular relationship between the cover and the cam. The components are of moulded plastics material, whereby the cam member can be fitted to the body from within by flexure of the latter's walls and the cover can be sprung over the spigots. This arrangement closes the body except at (i.) the mouthpiece, (ii.) an upper opening 110 to which a medicament can 111 is fitted and (iii.) air inlets 112, covered by the cover when in its closed position over the mouthpiece.

The can is held in the opening 110 by detents 114 moulded inside the opening and engaging in a groove 115 formed in the can for retaining its closure collar. Thus the can and the body 101 are rigidly connected. Also moulded inside the body are ribs 116 axially aligned with the detents. A junction member 117 is slidably accommodated in the body with the ribs engaging in grooves 118 in its periphery.

Centrally, the junction member has a socket 120 for an outlet stem 121 of the can. The socket is continued by a passage 122, which has a thin wall, kinkable portion 123 and a nozzle end 124. This is in a movable outlet member 125 of a valve part of the junction member. The main part of the junction member 117 and the outlet member are connected by a living hinge 126. The outlet member has a depending lug 127 for engagement with a cam to be described and a breath actuation flap 128.

To either side of the valve portion of the junction member, it has two depending fingers 130. These abut—under the force of the internal spring (not shown) of the can—two spaced, main cam lobes 131 on the cam member 105. A secondary cam lobe 132 is arranged between the main lobes.

The action of the dispenser is as follows:

The cam member and the cover are assembled to body in the closed position; the can stem is fitted to the junction member; and this sub-assembly is introduced into the upper opening 110. With the ribs 116 engaged in the grooves 118, the can is forced in until the detents 114 engage in the groove 115. Initially, the fingers 130 engage on a small radius portion of the cam lobes 131 and the depending lug 127 engages a small radius portion of the secondary lobe 132. There can be a small clearance between the lug 127 and the lobe 132, with the flap 128 engaging an internal stop 133 in the mouthpiece. This directs the nozzle 124 towards the (closed) mouthpiece.

On opening of the cover, by swinging about the axis of the cam member, the main lobes 131 lift the junction member and stem 121 towards the can. The secondary lobe acts on the lug 127 to move the outlet member to a position where the flap 128 is lifted and the kinkable portion 123 is closed. The cam timing is such that the flap is lifted prior to full lifting of the junction member. The latter has a C-shaped spring 135 and the outlet member has a pip 136, which co-operate in an over-centre manner to hold the flap up as the junction member is fully lifted. This releases a dose into the kinked valve, which retains it.

Breathing in through the mouthpiece draws air across the flap, that is round its edges from the air inlets 112, with a pressure differential developing. The over-centre spring retention of the flap is overcome and it is sprung down to dispense the dose as the outlet nozzle points into the mouthpiece. This, it is free to do since the lug is free of the secondary lobe at this position.

The mechanism is reset by closure of the cover over the mouthpiece. The junction member drops under the action of the can valve spring and control of the main cam lobes. The secondary cam lobe 132 and the flap lug 127 engage on their rear faces, that is the faces opposite from the those which cause lifting of the flap on opening of the cover. Such engagement is unwanted and the faces are provided with complementary wedge shapes 137,138, whereby the lobe and lug deflect sideways and pass each other. This deflection causes a drag on the lug and keeps the flap in its open position. To ensure that the lobe and lug re-engage for next use, each being thin for deflection, their front faces are provided with complementary V edge and groove formations 139,140.

The above embodiment has the advantages over conventional dispenser of the same general type—also known as pressurised metered dose inhalers—in which the can is depressible in the body, which extends along the greater part of the length of the can, of:

1. economising on use of plastics material, in that the major part of the can is not surrounded by a part of the body;
2. economising on labelling of the body in that the labelling of the can is exposed and does not require duplication.

Referring to FIG. 13 to FIG. 20, the dispenser thereshown has a body 201 with a mouthpiece 202 and a pivoted mouthpiece cover 203. The mouthpiece is formed as a aperture 2021 in a separate body part 2012 clipped to a main body part 2011. The main part 2011 has upper and lower grooves of which the lower 20131 only is shown and the mouthpiece part has upper and lower clips of which again only the lower 20132 is shown which engage in the grooves when the mouthpiece part is slid from below to engage with the main part. The mouthpiece part is cutaway 2014 with respect to the medicament can 211 fitted to the body, to define an air inlet exposed by the cover when this is open.

The cover is pivoted about an axis 204 low in the body at the joint between the two body parts. Integrally moulded with the cover 203 is a half round shaft 2031, which carries a cam arrangement 205. Whilst both of the body parts have semicircular scallops 2015,2016 to allow the shaft to pass and to provide some location, the primary location for the shaft in its function of reacting cam force is provided in scallops 2017 in flanges 2018 extending up from the end of the body. The flanges are integral with the main body part 2011 and extend into the space enclosed by the cover, so as to be able to support the shaft at the joint line between the parts.

The body parts 2011,2012, and the cover (with the shaft and cam arrangement) 203 are of moulded polypropylene material, whereby they can be fitted together with a modicum of flexure.

The cam arrangement 205 comprises a pair of cam lobes 2051,2052 and an intermediate shaft 2053.

The can 211 is held in an opening 210 at the upper end of the main body part 2011 by a pair of location pins 2101 in openings 2102 in sidewalls of the body part. The pins positively locate the can with respect to the body by engagement in a groove 215 formed in the can for retaining its closure collar. Thus the can and the body 201 are rigidly connected. Also moulded inside the body are internal ribs 216. A junction member 217 is slidably accommodated in the body with the ribs engaging in grooves 218 in its periphery. The junction member also is of moulded polypropylene.

Centrally, the junction member has a socket 220 for an outlet stem 221 of the can. The socket is continued by a passage 222, which has a thin wall, kinkable portion 223 and a nozzle end 224. This is in a movable outlet member 225 of a valve part 2172 of the junction member. The main part 2171 of the junction member 217 and the valve part 2172 are connected by a living hinge 226. To both sides of the outlet member are provided flats 2251, which form the base for a breath actuation flap 228, angled with respect the flats and connect to living hinge portions at the outside ends of the flats. A lug 227 depends from the outlet member for engagement with a cam finger 232 extending from between the pair of cam lobes 2051,2052.

To either side of the socket 220 of the junction member, it has two depending fingers 230 arranged to co-operate with cam lobes at their distal ends 2301. These abut—under the force of the internal spring (not shown) of the can, and with the interposition of two leaves 2019—the cam lobes 2051, 2052. The leaves extend in from extensions of the flanges 2018. The fingers have shaped portions 2302 on the flap side thereof with detents 2303 for engaging with the flap at the inward ends of the flats 2251. The junction member is moulded with the kinkable portion 223 straight and for use, the flap is pivoted to pass over the detents. The latter then form stops for the flap in its open position of the kink tube.

Additional features are a pair of spring fingers 2252 on the valve part 2172 to either side of the lug 227 and a pair of lugs 236 on the flats 2251 at the hinges. These co-operate with a pair of curved leaf springs 235 on the main part 2171 of the junction member. Further the shaft 2031 has discs 2032 outwards of the cam lobes with finger 2033 for co-operating with the fingers 2252.

The action of the dispenser is as follows:

The can is assembled to the junction member with the socket 220 receiving the stem 221; and the cover is assembled to the body part with the shaft journalled in the scallops. The junction member is slid into the main body part with ribs 216 engaging in the grooves 218 and the pins 2101 being inserted to retain the can. The flap is pivoted out over the detents 2303. The mouthpiece part can then be slid on and engaged with the cover fully open. The latter is closed. This assembly renders the dispenser ready for use.

The action of closing the cover causes the cam fingers 2033 to engage the flap fingers—should the flap be pivoted towards the can—and pivot the flap to its position in which the nozzle 224 towards the (closed) mouthpiece and the kink tube is unkinked. The distal ends 2301 of the fingers 230 of the junction member engage—with the interposition of the leaves 2019—on a small radius portion of the cam lobes 2051,2052 and the depending lug 227 is positioned in front of engages a small radius portion of the cam finger 232. The spring fingers 2252 engage the pair of lugs 236 to urge the flap to its position defined by the detents 2303.

On opening of the cover, by swinging about the axis of the cam member, the cam finger 232 acts on the lug 227 to move the outlet member to a position where the flap 228 is lifted and the kinkable portion 223 is closed. The cam timing is such that the flap is lifted before any other action. The lugs 236 pass over centre with respect to the spring fingers 2252. The latter urges the flap into abutment with a stop 238 formed on the main part 2171 of the junction member 217. In this position, the kink tube is kinked and will not pass a dose about to be released into it.

Further opening of the cover causes the cam lobes 2051, 2052 to lift the junction member and stem 221 towards the can. This releases a dose from the can into the kinked valve, which retains it. The cover stops by abutment with body and the mechanism is cocked and primed for use.

Breathing in through the mouthpiece draws air across the flap, that is round its edges from the air inlet 2014, with a pressure differential developing. The over-centre spring retention of the flap is overcome and it is sprung down to dispense the dose as the outlet nozzle points into the mouthpiece. This, it is free to do since the lug 227 is free of the cam finger 232 at this position.

Figure 12:
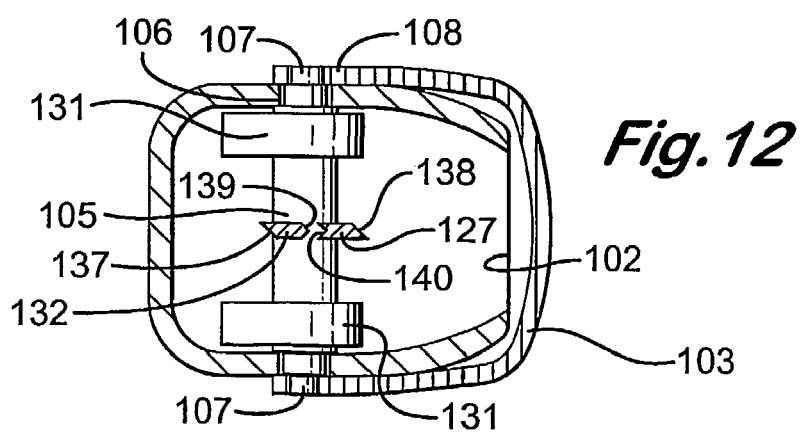
FIG. 12 is another cross-sectional view, this on the line XII—XII in FIG. 7.
Figure 13A:
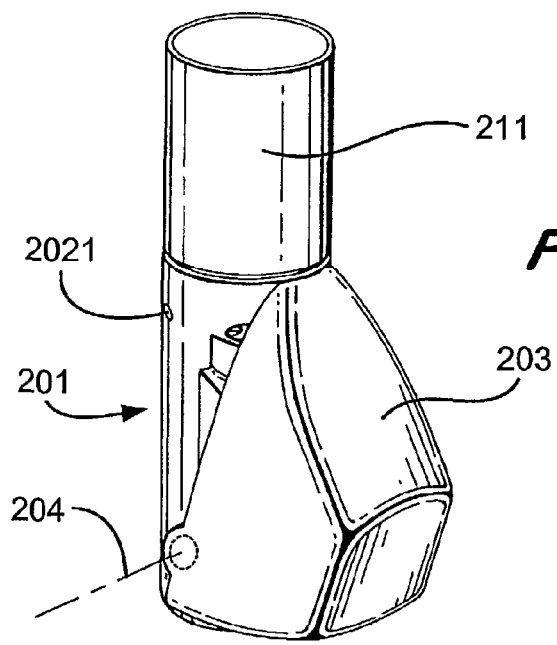
FIG. 13 shows in oblique side views (a) & (b) a third dispenser of the invention with its mouthpiece cover open and shut.
Figure 13B:
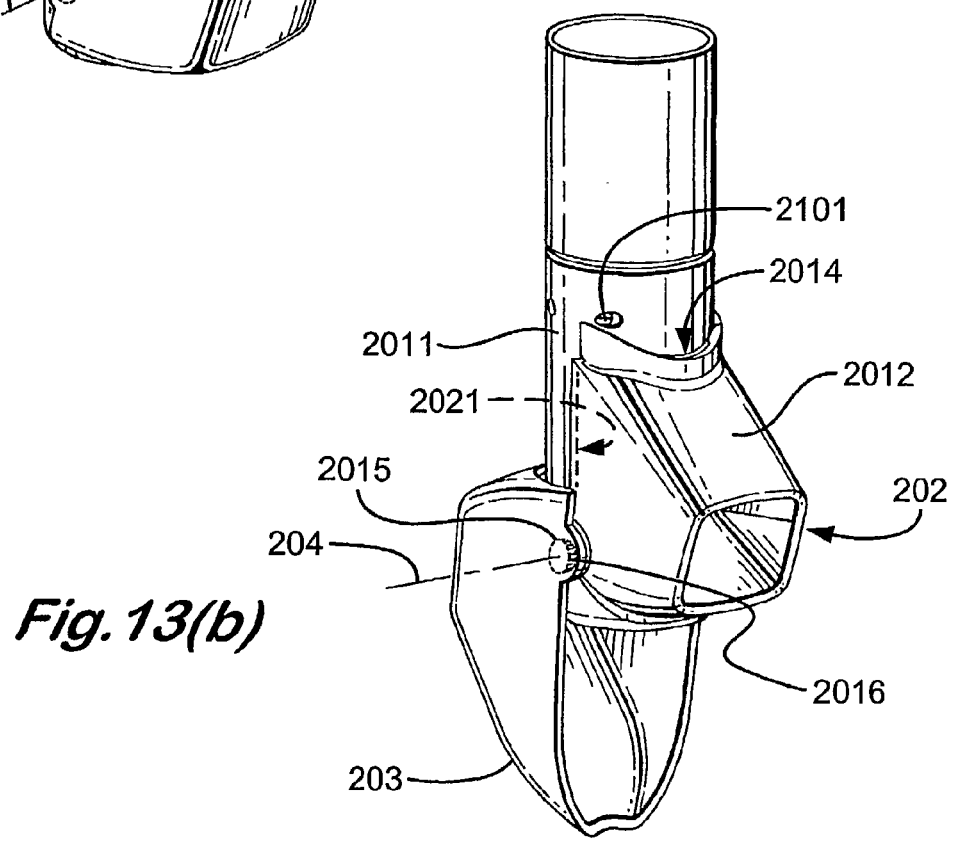
Figure 14:
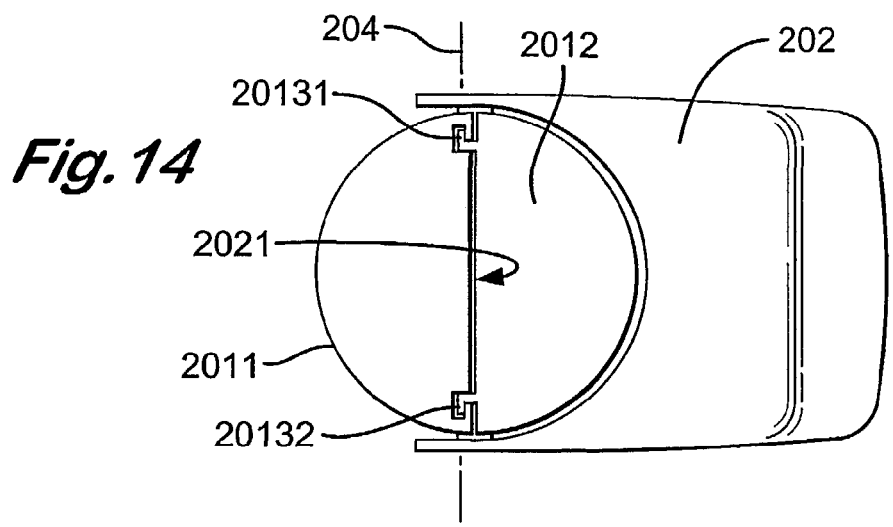
FIG. 14 is an underneath view of the dispenser when closed.
Figure 15:
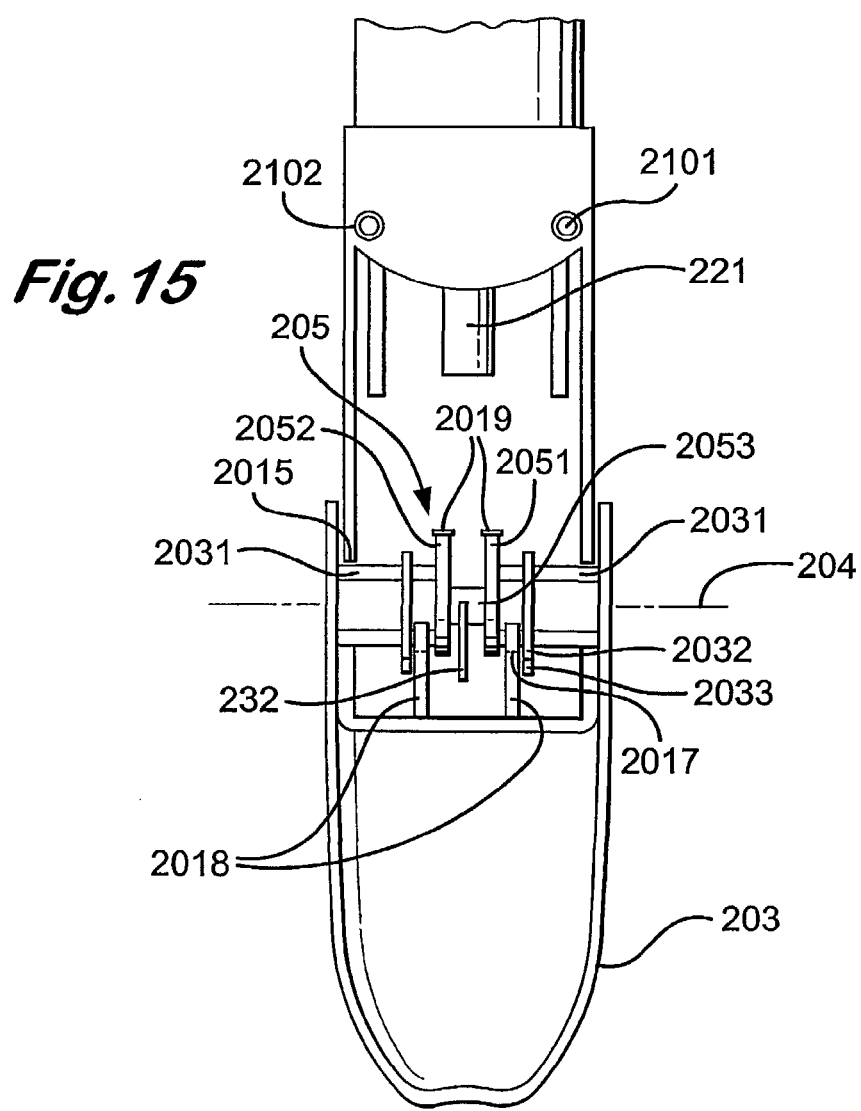
FIG. 15 is a front view of the third dispenser, with its mouthpiece and junction member removed, showing the cover open and the cam arrangements integral with the cover.
Figure 16A:
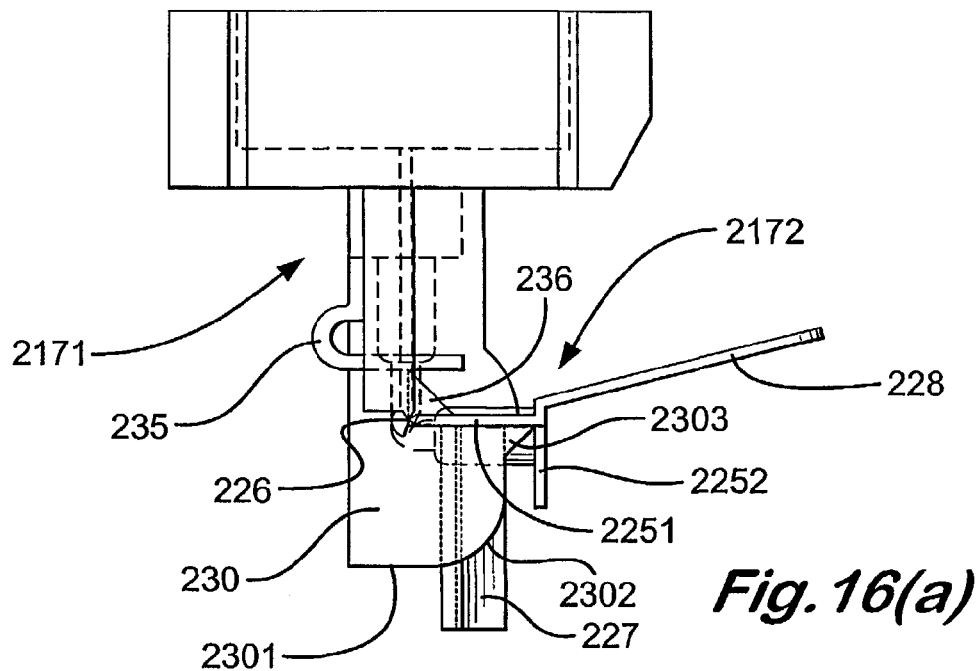
FIG. 16 shows in side and underneath views a movable junction member of the dispenser of FIG. 15.
Figure 16B:
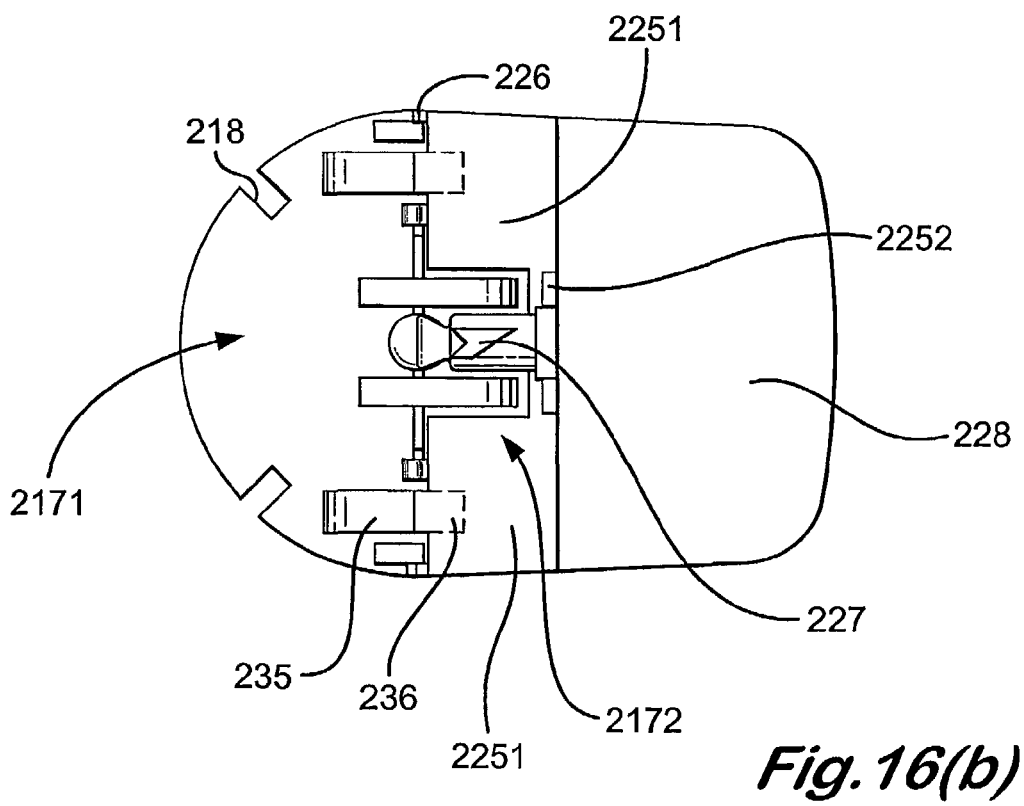
Figure 17A:
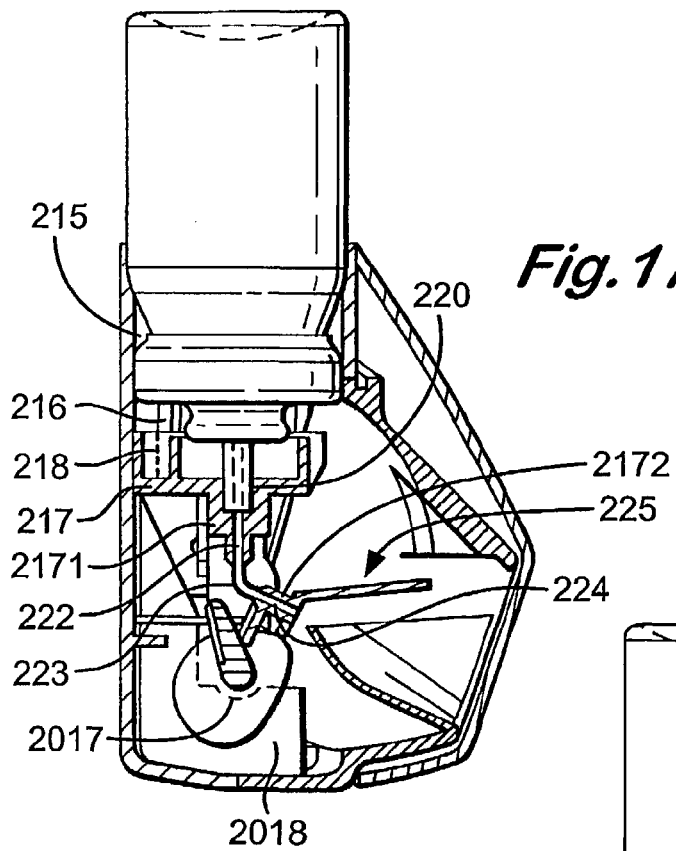
FIG. 17 shows in a series of cross-sectional side views (a) to (d) similar to FIG. 1 the third dispenser, in quiescent, cocked, charged and dispensed state.
Figure 17B:
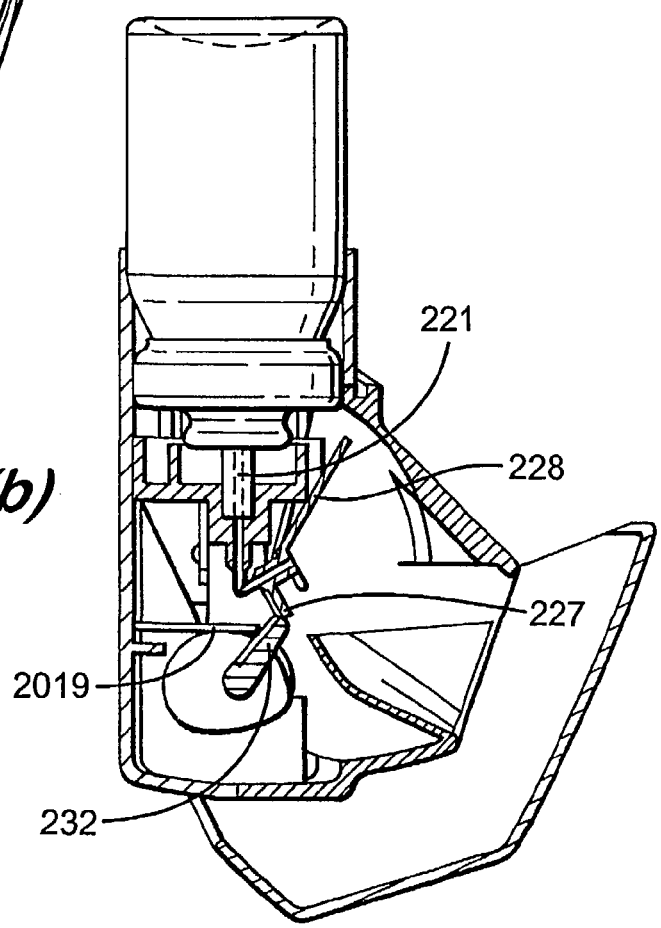
Figure 18:
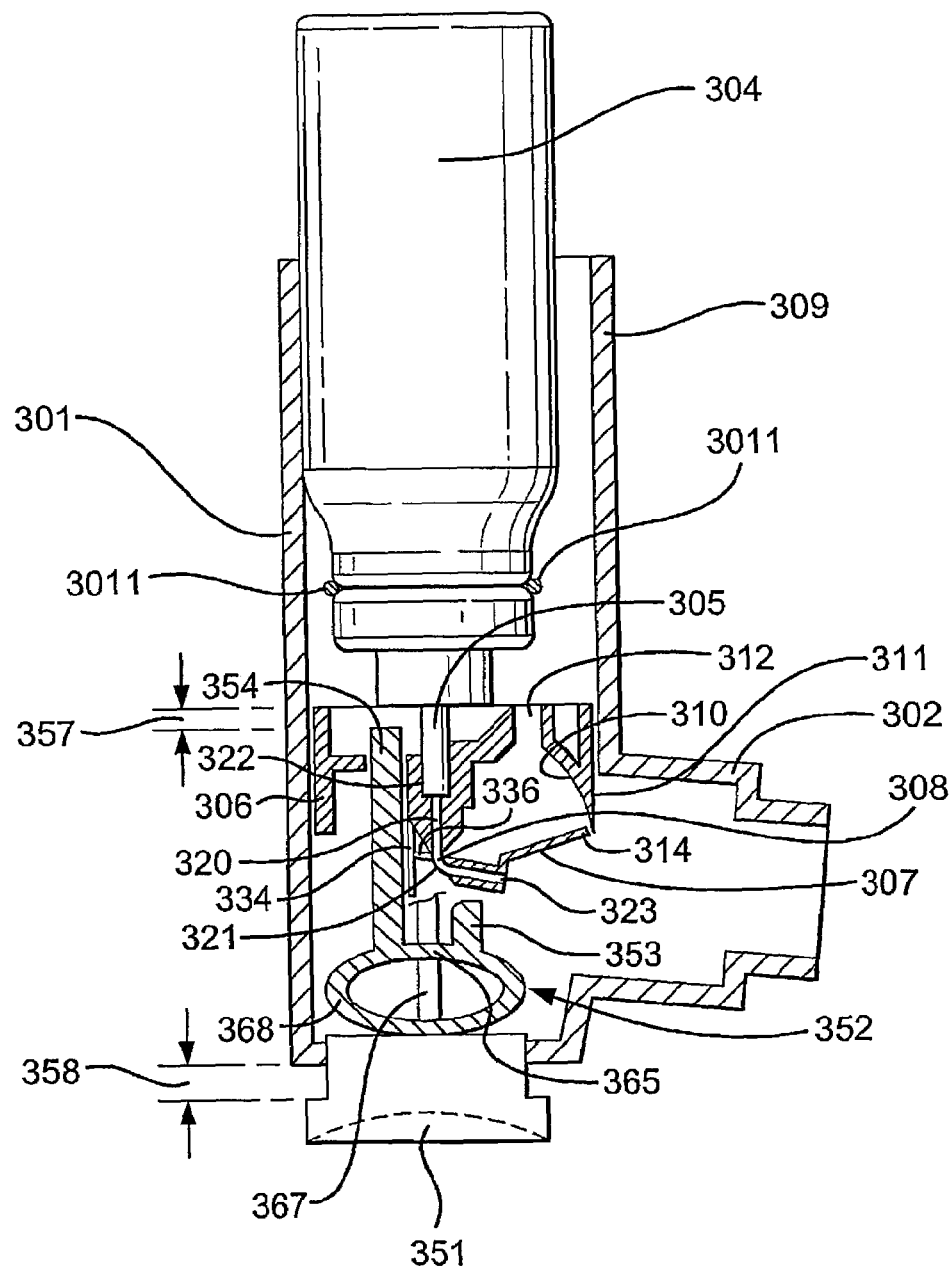
FIG. 18 is a cross-sectional side view of a fourth dispenser of the invention a normal state.

The mechanism is reset by closure of the cover over the mouthpiece. The junction member drops under the action of the can valve spring and control of the main cam lobes. The cam finger 232 and the flap lug 227 engage on their rear faces, that is the faces opposite from the those which cause lifting of the flap on opening of the cover. Such engagement is unwanted and the faces are provided with complementary wedge shapes—as shown in FIG. 12—whereby the lobe and lug deflect side ways and pass each other. This deflection causes a drag on the lug and keeps the flap in its open position. To ensure that the lobe and lug re-engage for next use, each being thin for deflection, their front faces are provided with complementary V edge.

Turning on to FIGS. 20 and 21, the embodiment thereshown has similarities to that of FIGS. 1 to 5, but in place of being operated by depression of the can 304, operation is by upwards action on a button 351. This dispenser has a body 301 with a mouthpiece 302. The aerosol drug can 304 is pinned 3011 in the body. The can has a dispensing spout 305, which engages a junction member 306, slidably mounted in the body and incorporating a breath movable flap 307 and a kink valve 308. The parts (other than the can) are of injection moulded plastics material.

The body has a D-shaped cross-section in plan, with the flat 309 of the D at the mouthpiece side 302, the latter being set up from the bottom of the body. The junction member 306 is of complementary shape and arranged to closely fit in the body. It has a curved under-contour 310 on the flat side 311 and a slot 312 adjacent the inner end of the flap.

The movable flap 307 is connected to the main receptor moulding part by a living hinge (not shown) arranged at the centre of curvature of the contour 310, whereby the distal edge 314 of the flap can move with a small clearance from the contour.

The junction member is moulded with the flap angled down with respect to the use orientation and a linear passage 320 through it. The central portion 321 of the passage has a thin wall thickness, whereby when the flap is hinged up, the passage kinks and closes. The upper end 322 of the passage is of larger diameter to receive the spout of the can. The lower end of the passage forms a spray nozzle 323, which is directed in accordance with the angle of the flap.

The junction member has two depending leaf springs 334, which abut lugs 336 on the flap for giving it an over-centre action.

Figure 19:
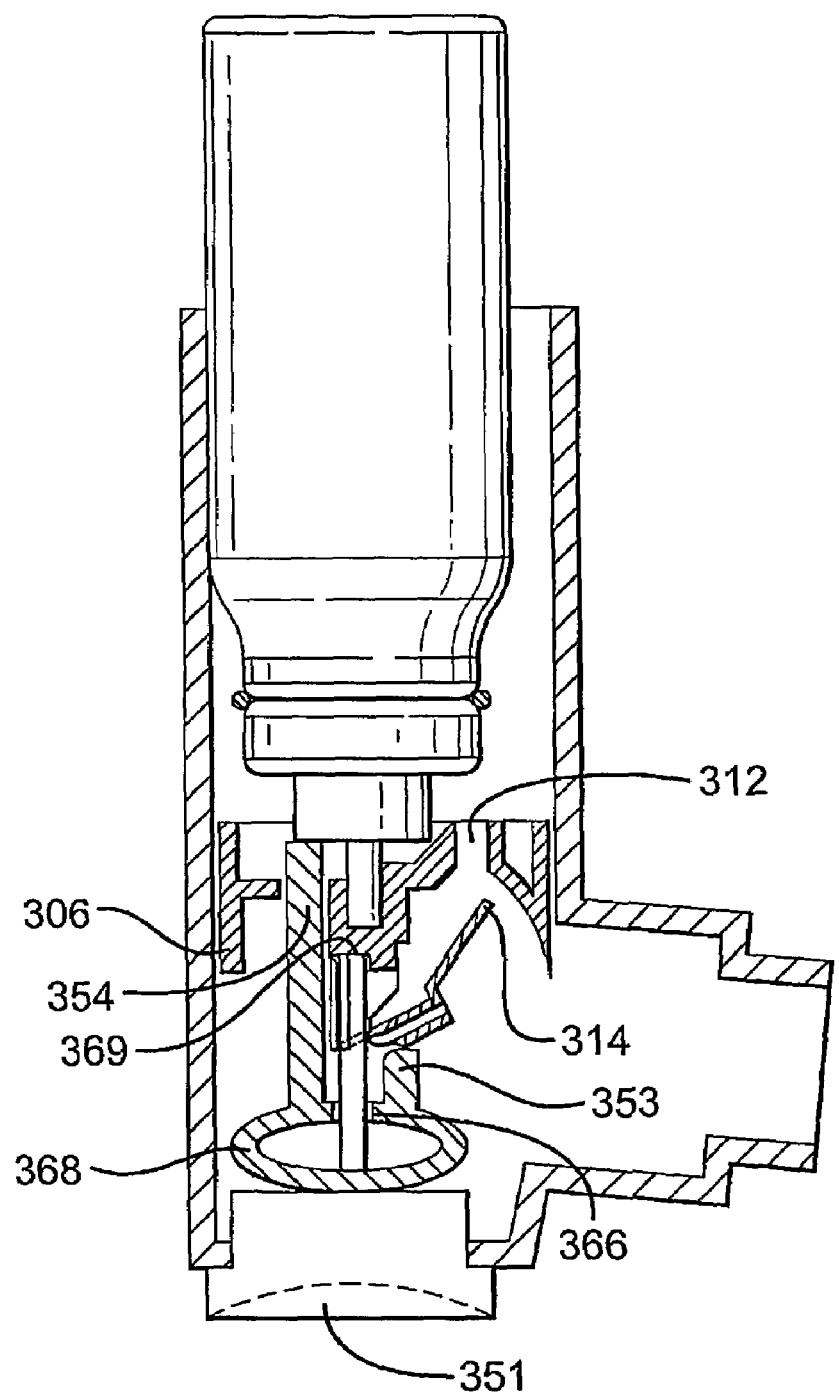
FIG. 19 is a similar view of the fourth dispenser, ready to release a dose, the cross-section partially deviating from the centre of the dispenser to show a finger moving a junction member of the device.

An actuating mechanism 352 is provided beneath the carrier and comprises two abutment fingers 353,354 and the actuation button 351. The fingers are interconnected by a yoke 365, which has a pair of apertures 366, through which two additional fingers 367 pass from the button. The fingers are positioned on opposite sides of the kink valve, as illustrated in FIG. 19. A spring 368 integral with the yoke 365 allows movement of the yoke on the fingers 367, i.e. movement further inwards of the button when the yoke is stopped. The length of the fingers is such that on initial movement towards the can of the button, the shorter finger 353 abuts the flap and moves it to kink its tube. This is illustrated in the FIG. 18, by the distance 357 between the end of the long finger 354 and the cap of the can being shorter than the travel 358 allowed between the button and the body.

The motion of the yoke is stopped by abutment of the long finger 354 on the cap of the can. The button can be moved in further with compression of the springs 368 and abutment of the additional fingers 367 on a flat 369 on the junction member, moving it towards the can. This action is against the can's spring and results in dispensing of a dose into the kink tube.

Inhalation draws the flap down, releasing the dose, with the flap being stopped in the desired position by the shorter finger 353. Release of the button allows return of the components to their original position.

The invention claimed is:

1. A dispenser for a gaseous, gas borne or droplet substance contained in a source thereof, the dispenser including:
   a body with a mouthpiece;
   a junction member in the body for the substance source; and
   a breath actuatable valve, for controlling the release of the gas or liquid containing or comprising the substance, the valve comprising:
      a flexible tube for receiving the said gas or liquid, the tube extending from a valve inlet connected to the junction member and having a portion which is kinkable for closure of the valve and movable to an open position in which the tube is un-kinked for opening of the valve; and
      a member arranged for movement in the body by inhalation to un-kink the valve;
   the tube being kinked to an obturating extent when the movable member is in a ready position and un-kinked when the movable member is moved on inhalation for release of the gas or liquid;
wherein:
   the movable member is or includes a flap arranged in the body for action of breath on it on inhalation;
   the junction member, the flexible tube and the movable flap are a single injection moulding of plastics material; and
   the movable flap is pivotally connected to the junction member.

2. A dispenser according to claim 1, wherein the movable flap is pivotally connected to the junction member by a living hinge which is an integral part of the single injection moulding.

3. A dispenser according to claim 1, wherein:
   the junction member is slidably mounted in the body for movement in a direction for dispensing a dose of the substance from the source and
   the dispenser includes:
      means for pivoting the flap to its ready position on or prior to initial movement of the junction member and junction member resilient means for returning the junction member after release of the dose.

4. A dispenser according to claim 1, wherein the dispenser includes means to hold the flap in its ready position prior to inhalation movement to un-kink the valve.

5. A dispenser according to claim 4, wherein the flap holding means is an over-centre mechanism.

6. A dispenser according to claim 5, wherein the over-centre mechanism comprises a lug and a spring, both integrally moulded with the said single injection moulding, one with the junction member and the other with the flap.

7. A dispenser according to claim 6, wherein the lug is integrally moulded with the flap for pivotal movement with it about the living hinge and the spring is integrally moulded with the junction member.

8. A dispenser according to claim 7, wherein the spring is a leaf spring normally urging the flap to an open position of the valve and urging the flap to its ready position when passed over-centre to this position.

9. A dispenser according to claim 1, wherein the single injection moulding is provided with formations guiding it for movement in the body.

10. A dispenser according to claim 1, wherein the single injection moulding is mounted in a carrier provided with formations guiding it for movement in the body.

11. A dispenser according to claim 3, wherein:
   the junction member resilient means is a spring in the source and
   the dispenser includes:
      means for locating the source in the body with the junction member being slidable towards it and
      means for displacing the junction member towards the source for dispensing the dose into the kinked tube.

12. A dispenser according to claim 11, wherein:
   the means for displacing the junction member comprises:
      a grippable member rotatably arranged on the body and
      a rotary-to-linear motion conversion mechanism, arranged to convert rotary motion of the grippable member to linear motion for displacing the junction member towards the source and
   the means for pivoting the flap is incorporated in the motion conversion mechanism.

13. A dispenser according to claim 12, wherein the grippable member is a cocking lever.

14. A dispenser according to claim 13, wherein the cocking lever is a cover for the mouthpiece prior to dispensing of a dose from the source, a dose being dispensed to the kink valve on opening of the cover.

15. A dispenser for a gaseous, gas borne or droplet substance contained in a source thereof, the dispenser including:
   a body with a mouthpiece;
   a junction member in the body for the substance source; and
   a breath actuatable valve, for controlling the release of the gas or liquid containing or comprising the substance, the valve comprising:
      a flexible tube for receiving the said gas or liquid, the tube extending from a valve inlet connected to the junction member and having a portion which is kinkable for closure of the valve and movable to an open position in which the tube is un-kinked for opening of the valve; and
      a member arranged for movement in the body by inhalation to un-kink the valve;
   the tube being kinked to an obturating extent when the movable member is in a ready position and un-kinked when the movable member is moved on inhalation for release of the gas or liquid;
   wherein the dispenser also includes:
      a spring for assisting the movement to un-kink the tube and
      means to hold the movable member in the ready position to close the tube by kinking prior to inhalation.

16. A dispenser according to claim 15, wherein the holding means is a frictional means holding the movable member ready for release and released by overcoming the frictional force holding the movable member in its ready position.

17. A dispenser according to claim 15, wherein the holding means is a mounting of the movable member in an over-centre manner with respect to the spring, whereby the spring acts to urge the movable member into the ready position when close to this position, and away from it when the inhalation force on the movable member causes the spring to pass over-centre after a small movement of the movable member to assist in the un-kinking.

18. A dispenser according to claim 15, wherein the movable member is translationally mounted in the body.

19. A dispenser according to claim 15, wherein the movable member is pivotally mounted in the body.

20. A dispenser according to claim 19, wherein the movable member is pivotally mounted in the body about a pivot fixed in the body.

21. A dispenser according to claim 19, wherein the movable member is pivotally mounted in the body about a pivot provided on a carrier, itself translationally mounted in the body.

22. A dispenser according to claim 19, wherein a stop is provided for stopping it in a position in which an outlet from the tube points directly out of the mouthpiece.

23. A dispenser according to claim 17, wherein the over-centre mechanism comprises a lug and a spring, both integrally moulded with a single injection moulding, one with the junction member and the other with a flap.

24. A dispenser for a gaseous, gas borne or droplet substance contained in a source thereof, the dispenser including:
   a body with a mouthpiece;
   a junction member in the body for the substance source; and
   a breath actuatable valve, for controlling the release of the gas or liquid containing or comprising the substance, the valve comprising:
      a flexible tube for receiving the said gas or liquid, the tube extending from a valve inlet connected to the junction member and having a portion which is kinkable for closure of the valve and movable to an open position in which the tube is un-kinked for opening of the valve; and
      a member arranged for movement in the body by inhalation to un-kink the valve;
   the tube being kinked to an obturating extent when the movable member is in a ready position and un-kinked when the movable member is moved on inhalation for release of the gas or liquid;
   wherein the dispenser also includes:
      means for locating the source in the body with the junction member being slidable towards it and
      means to cock the breath actuatable valve to a condition in which the movable member is moved to the ready position, the cocking means including:
         a cocking lever pivotally mounted on the body and operatively connected to the movable member.

25. A dispenser according to claim 24, wherein the cocking lever is arranged to move the junction member for dispensing of the substance to the valve.

26. A dispenser according to claim 24, wherein the cocking lever is a trigger arranged to be squeezed when the dispenser is to be used.

27. A dispenser according to claim 24, wherein the cocking lever is a cover for the mouthpiece prior to dispensing of a dose from the source, a dose being dispensed to the kink valve on opening of the cover.

28. A dispenser according to claim 24, wherein the cocking lever incorporates a main cam arranged to co-operate with the junction member.

29. A dispenser according to claim 28, further comprising means for pivoting a flap comprising a secondary cam mechanism acting between the cocking lever and the flap.

30. A dispenser according to claim 29, wherein the secondary cam mechanism comprises a finger on the cam of the cocking lever and a finger on the flap, the fingers engaging as the cocking lever is opened to move the flap to its ready position.

31. A dispenser according to claim 30, wherein the fingers are shaped to deflect away from each other on return movement of the cocking lever, with the flap in its position corresponding to the valve being open.

32. A dispenser according to claim 30, including a tertiary cam mechanism for returning the flap to its valve open position on return movement of the cocking lever.

33. A dispenser according to claim 32, wherein the tertiary cam mechanism comprises a finger on the cocking lever and a finger on the flap, the fingers engaging as the cover is closed to move the flap to its valve open position if not already in this position.

34. A dispenser according to claim 28, wherein the body includes one or more webs extending between the main cam and the junction member for creating a lateral cam force and transmitting longitudinal cam force to the junction member.

35. A dispenser according to claim 28, wherein the cocking lever includes a shaft having the main cam formed thereon, the shaft being of hollow half-round configuration and wherein the body includes at least one partially open journal for the half-round shaft.

36. A dispenser according to claim 24, wherein the body includes a secondary body part attachable to a main body part to provide the mouthpiece and an air inlet between the two parts.

37. A dispenser for a gaseous, gas borne or droplet substance contained in a source thereof, the dispenser including:
   a body with a mouthpiece;
   a junction member in the body for the substance source; and
   a breath actuatable valve, for controlling the release of the gas or liquid containing or comprising the substance, the valve comprising:
     a flexible tube for receiving the said gas or liquid, the tube extending from a valve inlet connected to the junction member and having a portion which is kinkable for closure of the valve and movable to an open position in which the tube is un-kinked for opening of the valve; and
     a member arranged for movement in the body by inhalation to un-kink the valve;
   the tube being kinked to an obturating extent when the movable member is in a ready position and un-kinked when the movable member is moved on inhalation for release of the gas or liquid;
wherein:
   the junction member is slidably mounted in the body for movement in a direction for dispensing a dose of the substance from the source against resilient urging of a spring in the source and
   the dispenser includes:
     means for locating the source in the body with the junction member being slidable towards it,
     means for pivoting a flap to its ready position on or prior to initial movement of the junction member,
     a button arranged on the body opposite the source and movable towards the source with abutment against the junction member and with compression of the spring in the source for displacing the junction member towards the source for dispensing the dose into the kinked tube and
   an actuator having:
     an first abutment movable with the button against the flap for pivotal movement of the flap on initial movement of the button;
     a second abutment movable with the first abutment against a fixed point in the dispenser for limiting the movement of the first abutment member and
     a spring acting between the button and the abutments for causing the limited movement of the latter on movement of the button and allowing further movement of the button for movement of the junction member for dispensing a dose into the tube kinked on its pivotal movement.

38. A dispenser according to claim 37, wherein the abutments are so arranged that the first abutment is moved at the end of its limited movement to a position in which it acts as a stop for the flap on its return pivotal movement for release of the dose on inhalation.

39. A dispenser according to claim 37, wherein the actuator is a single injection moulding.

40. A dispenser according to claim 24 and a source of the substance for use by the dispenser, wherein the source of the substance includes a metered dose valve, whereby the metered dose value releases a metered dose each time the dispenser is operated.

41. A dispenser according to claim 24 and a source of the substance for use by the dispenser, wherein the source includes a non-metered dose valve, the dose being metered by the capacity of the breath actuatable valve.

* * * * *